(12) United States Patent
Peng et al.

(10) Patent No.: US 11,384,327 B2
(45) Date of Patent: Jul. 12, 2022

(54) MICROFLUIDIC DEVICES AND METHODS FOR PURIFYING RARE ANTIGEN-SPECIFIC T CELL POPULATIONS

(71) Applicants: California Institute of Technology, Pasadena, CA (US); Gwangju Institute of Science and Technology (GIST), Gwangju (KR)

(72) Inventors: Songming Peng, Pasadena, CA (US); James R. Heath, Pasadena, CA (US); William Chour, Pasadena, CA (US); Alphonsus Hon-Chung Ng, Pasadena, CA (US); Sung Yang, Gwangju (KR); Jongchan Choi, Gwangju (KR); Ji-Chul Hyun, Gwangju (KR)

(73) Assignees: California Institute of Technology, Pasadena, CA (US); Gwangju Institute of Science and Technology (GIST), Buk-gu (KR)

( * ) Notice: Subject to any disclaimer, the term of this patent is extended or adjusted under 35 U.S.C. 154(b) by 327 days.

(21) Appl. No.: 16/347,559

(22) PCT Filed: Nov. 1, 2017

(86) PCT No.: PCT/US2017/059598
§ 371 (c)(1),
(2) Date: May 3, 2019

(87) PCT Pub. No.: WO2018/085453
PCT Pub. Date: May 11, 2018

(65) Prior Publication Data
US 2020/0040293 A1    Feb. 6, 2020

Related U.S. Application Data

(60) Provisional application No. 62/424,652, filed on Nov. 21, 2016, provisional application No. 62/415,696, filed on Nov. 1, 2016.

(51) Int. Cl.
*C12M 3/06* (2006.01)
*B01L 3/00* (2006.01)
(Continued)

(52) U.S. Cl.
CPC ......... *C12M 23/16* (2013.01); *B01F 25/4331* (2022.01); *B01F 33/30* (2022.01);
(Continued)

(58) Field of Classification Search
CPC ............... B01F 13/0059; B01F 5/0647; B01L 2200/0652; B01L 2200/0668;
(Continued)

(56) References Cited

U.S. PATENT DOCUMENTS 7,150,812 B2   12/2006   Huang et al.
7,318,902 B2   1/2008    Oakey et al.
(Continued)

FOREIGN PATENT DOCUMENTS

WO   WO 99/09042        2/1999
WO   WO 2012/094642 A2  7/2012

OTHER PUBLICATIONS

Fritsch et al., "HLA-Binding Properties of Tumor Neoepitopes in Humans", Cancer Immunol Res; vol. 2, No. 6, Jun. 2014.
(Continued)

*Primary Examiner* — Jennifer Wecker
*Assistant Examiner* — Jonathan Bortoli
(74) *Attorney, Agent, or Firm* — Knobbe, Martens, Olson & Bear, LLP

(57) ABSTRACT

Disclosed herein are methods and devices for antigen-specific T cell identification or neoantigen identification. Also disclosed herein are devices for separating and isolating antigen-specific T cells or other particles of a certain size from a population of particles of different sizes. Also describe herein are methods and devices for the separation
(Continued)

and isolation of barcoded T cells from other nanoparticles containing barcodes for subsequent analysis and further processing of a viable T cell.

19 Claims, 20 Drawing Sheets

(51) Int. Cl.
*G01N 33/569* (2006.01)
*B01F 25/433* (2022.01)
*B01F 33/30* (2022.01)

(52) U.S. Cl.
CPC .. *B01L 3/502761* (2013.01); *G01N 33/56977* (2013.01); *B01L 2200/0652* (2013.01); *B01L 2200/0668* (2013.01); *B01L 2300/0654* (2013.01); *B01L 2300/0816* (2013.01); *B01L 2300/0864* (2013.01); *B01L 2300/0883* (2013.01); *B01L 2400/086* (2013.01)

(58) Field of Classification Search
CPC ..... B01L 2300/0654; B01L 2300/0816; B01L 2300/0864; B01L 2300/0883; B01L 2400/086; B01L 3/502761; C12M 23/16; G01N 33/56977
See application file for complete search history.

(56) References Cited

U.S. PATENT DOCUMENTS

| | | | |
|---|---|---|---|
| 7,472,794 B2 | 1/2009 | Oakey et al. | |
| 7,735,652 B2 | 6/2010 | Inglis et al. | |
| 7,988,840 B2 | 8/2011 | Huang et al. | |
| 8,021,614 B2 | 9/2011 | Huang et al. | |
| 8,282,799 B2 | 10/2012 | Huang et al. | |
| 8,304,230 B2 | 11/2012 | Toner et al. | |
| 8,394,590 B2 | 3/2013 | Kwong et al. | |
| 8,579,117 B2 | 11/2013 | Loutherbeck et al. | |
| 2007/0264675 A1* | 11/2007 | Toner | B01L 3/502753 435/7.23 |
| 2008/0023399 A1* | 1/2008 | Inglis | G01N 33/54366 210/649 |
| 2012/0115755 A1 | 5/2012 | Oh et al. | |
| 2013/0098813 A1* | 4/2013 | Loutherback | G01N 30/6095 209/675 |
| 2013/0302883 A1* | 11/2013 | Fowler | B01L 3/502761 435/287.2 |
| 2014/0320849 A1* | 10/2014 | Chou | B03C 5/026 356/72 |
| 2015/0018226 A1 | 1/2015 | Hansen et al. | |
| 2015/0260711 A1* | 9/2015 | Toner | C12N 5/0087 156/278 |
| 2016/0121331 A1 | 5/2016 | Kapur et al. | |
| 2017/0003288 A1 | 1/2017 | Heath et al. | |
| 2018/0207639 A1* | 7/2018 | Butler | G01N 1/4077 |

OTHER PUBLICATIONS

Novak et al., "MHC class II tetramers identify peptide-specific human CD4+ T cells proliferating in response to influenza A antigen", J Clin Invest. 1999, vol. 104, No. 12, pp. R63-R67.
Sambrook et al., Molecular Cloning: A Laboratory Manual (2nd Edition, 1989).
Bakker et al., "Conditional MHC class I ligands and peptide exchange technology for the human MHC gene products HLA-A1,-A3,-A11, and -67", *PNAS*, vol. 105, No. 10, Mar. 11, 2008; pp. 3825-3830.
Carey et al., *Advanced Organic Chemistry*, Third Edition, University of Virginia, Charlottesville, Virginia, Plenum Press, 1991, preface/table of contents, in 53 pages.
Colowick, et al., eds., *Methods in Enzymology*, vol. I, McCollum-Pratt Institute, The Johns Hopkins University, Baltimore, Maryland, table of contents, Academic Press, Inc., in 2 pages.
Creighton, *Proteins: Structures and Molecular Properties* (W. H. Freeman and Company, 1993).
Fiorini et al., "Disposable microfluidic devices: fabrication, function, and application", *BioTechniques*, vol. 38, No. 3, 2005; pp. 429-446.
Herold et al., eds., "Lab on a Chip Technology", Caister Academic Press Norfolk UK (2009).
Inglis et al., "Critical particle size for fractionation by deterministic lateral displacement", *Lab Chip*, 2006; pp. 655-658.
International Search Report dated Mar. 6, 2018 in Application No. PCT/US17/59598 in 5 pages.
Lehninger, Biochemistry (Worth Publishers, Inc., $2^{nd}$ Ed. 1975).
Remington's Pharmaceutical Sciences, 18th Edition (Easton, Pennsylvania: Mack Publishing Company, 1990).
Toebes et al., "Design and use of conditional MHC class I ligands", *Nature Medicine*, vol. 12, No. 2, Feb. 2006; pp. 246-251.
Tsao et al., "Bonding of thermoplastic polymer microfluidics", *Microfluid Nanofluid*, vol. 6, 2009; pp. 1-16.
Yang et al., "Microfluidic Device Fabrication by Thermoplastic Hot-Embossing", *Microfluidic Diagnostics*, Humana Press, Totowa, NJ, 2013; pp. 115-123.
Yussuf et al., "Sealing and Bonding Techniques for Polymer-Based Microfluidic Devices", *Industrial Research Institute Swinburne (IRIS)*, Aug. 2001 (2007), in 8 pages.
File History of U.S. Appl. No. 12/901,151.
File History of U.S. Appl. No. 15/170,919.

* cited by examiner

MICROFLUIDIC DEVICES AND METHODS FOR PURIFYING RARE ANTIGEN-SPECIFIC T CELL POPULATIONS

CROSS-REFERENCE TO RELATED APPLICATIONS

This application is the U.S. national phase application under 35 U.S.C. § 371 of International Application No. PCT/US2017/059598, filed Nov. 1, 2017, which claims the benefit of U.S. Provisional Application No. 62/415,696, filed Nov. 1, 2016, and U.S. Provisional Application No. 62/424,652, filed Nov. 21, 2016. The contents of each of these Related Applications are incorporated by reference in their entirety.

STATEMENT REGARDING FEDERALLY SPONSORED RESEARCH OR DEVELOPMENT

This invention was made with government support under Grant No. CA199090 awarded by the National Institutes of Health. The government has certain rights in the invention.

BACKGROUND

It is becoming increasingly important to identify particularly rare antigen-specific T cells in challenging biological samples, such as tumor infiltrating lymphocytes. In such a situation, the biological sample itself may contain a relatively small number of cells ($10^4$), of which only a handful (<10) are the cells of interest. This is a regime where methods such as flow cytometry do not work well. A specific example is the analysis of populations of neoantigen-specific T cells from tumor infiltrates or peripheral blood. The analysis of such T cells can inform the construction of personalized cancer vaccines, or T cell receptor (TCR)-engineered T cell immunotherapies. What is needed, therefore, are new methods and devices for the separation and analysis of antigen-specific T cells.

SUMMARY OF THE INVENTION

According to some embodiments, provided herein is a microfluidic device comprising: a sample inlet; a separation channel comprising an array of obstacles disposed within the separation channel, wherein said array of obstacles comprises a plurality of rows of obstacles and a plurality of columns of obstacles, said plurality of rows of obstacles extending at an angle relative to the average flow direction of said separation channel; one or more capture areas each comprising one or more capture channels, wherein each capture channel comprises a trap region and an outflow region, wherein the width of the trap region is greater than a width at the outflow region; and an outlet; wherein the separation channel is disposed between and in fluidic communication with the sample inlet and the one or more capture areas, and wherein the one or more capture areas is disposed between and in fluidic communication with the separation channel and the outlet.

In some embodiments, the array of obstacles is adapted to separate particles having a size at or above a critical size from particles having a size less than the critical size in a flow of a heterogeneous fluid sample through the separation channel. In some embodiments, the plurality of obstacles is adapted to separate nanoparticles bound to T cells from unbound nanoparticles upon flow of a sample through said separation channel.

In some embodiments, the array of obstacles is configured to deflect said particles having a size at or above the critical size towards a first wall of said microfluidic channel. In some embodiments, the array of obstacles is configured to deflect particles having a size less than a critical size towards a second wall of said microfluidic channel opposite from said first wall, wherein the separation channel is bounded by said first wall and said second wall. In some embodiments, the array of obstacles are fixed in position and separated by gaps arranged so that the particles having a size at or above the critical size deflect towards a first wall of said separation channel during flow of said heterogeneous fluid sample through said separation channel. In some embodiments, the obstacles are I-shaped.

In some embodiments, the angle relative to the average flow direction of the separation channel is about 1 degree to about 15 degrees, from about 3 degrees to about 12 degrees, from about 4 degrees to about 8 degrees, or from about 5 degrees to about 7 degrees. In some embodiments, the angle relative to the average flow direction of the separation channel is about 6 degrees. In some embodiments, the angle relative to the average flow direction of the separation channel is about 3 degrees, 4 degrees, 5 degrees, 6 degrees, 7 degrees, 8 degrees, 9 degrees, or 10 degrees.

In some embodiments, the plurality of rows of obstacles comprises a gap between adjacent rows of from about 8 µm to about 15 µm. In some embodiments, the plurality of columns of obstacles comprise a gap between adjacent columns of from about 8 µm to about 15 µm.

In some embodiments, the microfluidic device further comprises a mixing channel disposed between and in fluidic communication with the separation channel and the one or more capture areas. In some embodiments, the mixing channel is serpentine-shaped.

In some embodiments, the microfluidic device further comprises a disbursement channel disposed between and in fluidic communication with the mixing channel and the one or more capture areas. In some embodiments, the disbursement channel comprises a branched network of channels extending from the mixing channel into two or more channels comprising said one or more capture areas.

In some embodiments, the microfluidic device further comprises a buffer inlet disposed adjacent to said sample inlet and in fluidic communication with said separation channel.

In some embodiments, the one or more capture areas are disposed at bends along a serpentine-shaped channel of said microfluidic device. In some embodiments, the one or more capture areas are disposed at bends along a plurality of serpentine-shaped channels of said microfluidic device.

In some embodiments, the separation channel flows into two distinct flowpaths, each comprising a mixing channel, a distribution channel, and said one or more capture areas. In some embodiments, the critical size is a diameter from 2 to 6 µm.

In some embodiments, the trap region of said capture channel comprises a width of about 12 µm, from 10 to 14 µm, from 8 to 16 µm, or from 8 to 12 µm. In some embodiments, the trap region is adapted to capture a T cell. In some embodiments, the outflow region of said capture channel comprises a width at or below about 4 µm, 3.5 µm, 3 µm, 2.5 µm, or 2 µm. In some embodiments, the outflow region of said capture channel comprises a width of about 2 µm. In some embodiments, the outflow region of said capture channel comprises a length of about 8-15 µm. In some embodiments, the outflow region is adapted to allow flow of fluid through said flow channel and prevent flow of a T cell captured in said trap region through said capture channel In some embodiments, the microfluidic device further comprises a sensor for detecting a signal from said trap region of said capture channel. In some embodiments, the signal is an optical signal or an electrical signal.

In some embodiments, the microfluidic device further comprises a cell prefocusing region adapted to disperse particles in a fluid flowing through said microfluidic device having a size at or above a critical size in a differential manner deviating from the direction of fluid flow towards said one or more capture channels.

In some embodiments, provided herein is a microfluidic device comprising: a sample inlet; a separation channel comprising an array of obstacles disposed within the separation channel, wherein said array of obstacles comprises a plurality of rows of obstacles and a plurality of columns of obstacles, said plurality of rows of obstacles extending at an angle of about 6 degrees relative to the average flow direction of said separation channel and comprising a gap between adjacent obstacles of from about 8 µm to about 15 µm, and said plurality of columns of obstacles comprising a gap between adjacent obstacles of from about 8 µm to about 15 µm; a serpentine-shaped mixing channel; a disbursement channel; one or more cell isolation channels comprising one or more capture areas each comprising one or more capture channels, wherein each capture channel comprises a trap region and an outflow region, wherein the width of the trap region is about 12 µm, the width of the outflow region is about 2 µm, and the length of the outflow region is about about 8-15 µm, wherein said trap region of said capture channel is configured to capture a T cell from a sample fluid flowing through said capture channel, and wherein said outflow region is configured to allow flow of said sample fluid through said capture channel, but to prevent flow of said T cell through said outflow region of said capture channel; and an outlet; wherein the separation channel is disposed between and in fluidic communication with the sample inlet and the one or more capture areas, wherein the serpentine-shaped mixing channel is disposed between and in fluidic communication with the separation channel and disbursement channel, wherein the disbursement channel comprises a branched network of channels extending from the mixing channel or the separation channel into two or more cell isolation channels or two or more mixing channels, and wherein the one or more cell isolation channels are disposed between and in fluidic communication with the separation channel and the outlet.

In some embodiments, the obstacles are I-shaped. In some embodiments, the one or more capture channels within said capture area are arranged as a linear array.

Also provided herein, according to some embodiments, is a method for separating and trapping particles above a critical size, the method comprising: applying a sample fluid comprising particles to a sample inlet of a device; separating particles at or above said critical size from particles below said critical size by flowing said sample through a first channel in said device comprising a separation channel, wherein said separation channel comprises an array of obstacles bounded by a first wall and a second wall, wherein said array of obstacles, in response to the flow of said sample fluid through said separation channel, laterally displaces said particles at or above said critical size within said array towards said first wall, such that said particles at or above said critical size flow towards a second channel in fluidic communication with said first channel along said first wall; and flowing said sample fluid comprising said particles at or above said critical size into said second channel, wherein said second channel comprises one or more capture areas each comprising one or more capture channels, wherein each capture channel comprises a trap region and an outflow region, wherein said flow induces movement of a single one of said particles at or above said critical size into said trap region, and wherein said outflow region allows fluid from said sample to flow through said capture channel, but prevents said particle at or above said critical size from moving through said outflow region, thereby trapping said particle at or above said critical size in said trap region of said capture channel.

In some embodiments, the particles having a size at or above said critical size comprise cells bound to one or more nanoparticles, and wherein said particles less than a critical size comprise unbound nanoparticles. In some embodiments, the particle further comprises a barcode encoding an identity of said particle.

In some embodiments, the cells bound to one or more nanoparticles are separated from unbound nanoparticles in said separation channel. In some embodiments, the nanoparticle comprises a bead. In some embodiments, the bead comprises a magnetic bead. In some embodiments, the cell is a T cell.

In some embodiments, the method for separating and trapping particles above a critical size further comprises determining the identity of the particle in said particle trap by determining a sequence of said barcode.

In some embodiments, the method for separating and trapping particles above a critical size further comprises contacting said barcode with one or more detectable probes to determine the identity of said particle. In some embodiments, the barcode is contacted with said one or more detectable probes in situ in said trap region.

In some embodiments, the method for separating and trapping particles above a critical size is performed using an embodiment of a microfluidic device as provided herein.

Also provided herein is a method for separating and trapping a nanoparticle-bound T cell, the method comprising: applying a sample fluid comprising nanoparticles and T cells to a sample inlet of a microfluidic device, wherein said nanoparticles consist of T cell-bound nanoparticles and unbound nanoparticles; separating bound T cell-bound nanoparticles from said unbound nanoparticles by flowing said sample fluid through a first channel in said microfluidic device comprising a separation channel, wherein said separation channel comprises an array of obstacles, wherein said array of obstacles, in response to the flow of said sample fluid through said separation channel, laterally displaces said T cell-bound nanoparticles within said array towards said first wall, such that said T cell bound nanoparticles flow towards a second channel, and flowing said sample fluid comprising said T cell-bound nanoparticles into said second channel, wherein said second channel comprises one or more capture areas each comprising one or more capture channels, wherein each capture channel comprises a trap region and an outflow region, wherein said flow induces movement of a single T cell bound to one or more of said T cell-bound nanoparticles into said trap region, and wherein said flow channel allows fluid from said sample to flow through said capture channel, but prevents said single T cell from passing through said outflow region, thereby trapping said single T cell in said particle trap.

In some embodiments, the nanoparticles are beads. In some embodiments, the beads are magnetic beads. In some embodiments, the nanoparticles each comprise a barcode.

In some embodiments, the nanoparticles are bound to an MHC-antigen complex, and wherein said barcode encodes the identity of said antigen. In some embodiments, the method for separating and trapping a nanoparticle-bound T cell further comprises determining the antigen-specificity of the single T cell in said particle trap by determining a sequence of said barcode.

In some embodiments, the method for separating and trapping a nanoparticle-bound T cell further comprises contacting said barcode with one or more detectable probes to determine the identity of said particle. In some embodiments, the barcode is contacted with said one or more detectable probes in situ in said trap region.

In some embodiments, the T cell is derived from a subject, and wherein the sequence of said barcode in said particle trap identifies the presence of a neoantigen in said subject. In some embodiments, the cell is derived from a patient, and wherein the sequence of said barcode in said particle trap identifies the presence of a T-cell receptor in said subject. In some embodiments, the T cell is derived from a patient, and wherein the sequence of said barcode in said particle trap identifies the presence of an antigen-specific T cell population in said subject.

In some embodiments, the method for separating and trapping a nanoparticle-bound T cell is performed using an embodiment of a microfluidic device as provided herein.

Also provided herein, according to some embodiments, is a method for identifying an antigen-specificity of a T cell in a population of T cells, the method comprising: providing a sample comprising one or more barcoded T cells and nanoparticles, wherein said nanoparticles are bound to an MHC-antigen complex and a barcode comprising a sequence encoding the identify of said antigen, wherein said nanoparticles consist of paired nanoparticles and unpaired nanoparticles, said paired nanoparticles bound to a T cell, and said unpaired nanoparticles not bound to a T cell, and wherein said one or more barcoded T cells are each bound to one or more of said paired nanoparticles; applying said sample to a sample inlet of a microfluidic device, said microfluidic device comprising: a first channel in fluidic communication with said sample inlet, said first channel comprising a separation channel, wherein said separation channel comprises an array of obstacles configured to laterally displace said one or more barcoded T cells from said unpaired nanoparticles towards a first wall upon flow of said sample through said separation channel, and a second channel in fluidic communication with said first channel along said first wall, said second channel comprises one or more capture areas each comprising one or more capture channels, wherein each capture channel comprises a trap region and a buffer outflow region; separating said barcoded T cells from said unpaired nanoparticles by flowing said sample through said array of obstacles from said sample inlet towards said second channel such that said barcoded cells are laterally displaced towards said first wall, such that said paired nanoparticles flow into said second channel; flowing one of said barcoded T cells into said trap region, wherein said buffer outflow region allows fluid from said sample to flow through said capture channel, but prevents said barcoded T cell from moving through said flow channel, thereby isolating said barcoded T cell in said trap region; contacting the barcode bound to the isolated barcoded T cell with one or more probes each comprising a detectable marker; and detecting one or more signals from said one or more probes, wherein said one or more signals is indicative of an antigen-specificity of said isolated barcoded T cell.

In some embodiments, the method for identifying an antigen-specificity of a T cell in a population of T cells further comprises comparing said one or more signals with a lookup table linking said one or more signals to an antigen, thereby determining an antigen-specificity of said isolated T cell. In some embodiments, the antigen is a neoantigen.

In some embodiments, the T cells are derived from a subject. In some embodiments, the subject has been diagnosed with cancer. In some embodiments, the one or more signals are used to determine the presence or absence of an antigen in the subject. In some embodiments, the antigen is a neoantigen. In some embodiments, the one or more signals are used to determine the presence or absence of a T cell receptor in the subject.

In some embodiments, the T cells have been enriched by said nanoparticles from a population of T cells. In some embodiments, the isolated barcoded T cell is viable.

In some embodiments, an opening of said capture channel into said trap region is situated along said first wall. In some embodiments, the unpaired nanoparticles are laterally displaced towards a second wall opposite of said first wall along said microfluidic channel. In some embodiments, the unpaired nanoparticles move along with the average the direction of flow of the microfluidic channel. In some embodiments, the unpaired nanoparticles are not laterally displaced towards said first wall. In some embodiments, the paired nanoparticles flow into said second channel along said first wall.

In some embodiments, the nanoparticles are beads. In some embodiments, the beads are magnetic beads.

In some embodiments, the method for identifying an antigen-specificity of a T cell in a population of T cells is performed using an embodiment of a microfluidic device as provided herein.

Also provided herein, according to some embodiments, is a microfluidic device comprising: a sample inlet; a separation channel adapted to disperse particles having a size at or above a critical size in a differential manner deviating from the average flow direction in a flow of a heterogeneous fluid sample through the separation channel; one or more capture areas, each comprising one or more capture channels comprising a trap region and an outflow region, said trap region adapted to capture at least one particle at or above a critical size from the fluid flowing through the capture area, and said outflow region adapted to allow flow of fluid through said capture channel channel and to prevent flow of said particle through said outflow region; and an outlet; wherein the separation channel is disposed between and in fluidic communication with the sample inlet and the one or more capture areas, and wherein the one or more capture areas is disposed between and in fluidic communication with the separation channel and the outlet.

In some embodiments, the separation channel is adapted to separate said particles having a size at or above said critical size from particles having a size less than the critical size in a flow of a heterogeneous fluid sample through the separation channel.

In some embodiments, the separation channel comprises an array of obstacles disposed within the separation channel. In some embodiments, the array of obstacles is configured to deflect said particles having a size at or above the critical size towards a first wall of said microfluidic channel. In some embodiments, the array of obstacles is configured to deflect particles having a size less than a critical size towards a second wall of said microfluidic channel opposite from said first wall, wherein the separation channel is bounded by said first wall and said second wall. In some embodiments, the array of obstacles are fixed in position and separated by gaps arranged so that the particles having a size at or above the critical size deflect towards a first wall of said separation channel during flow of said heterogeneous fluid sample through said separation channel. In some embodiments, the obstacles are I-shaped.

In some embodiments, the array of obstacles comprises a plurality of rows of obstacles extending at an angle relative to the average flow direction of said separation channel. In some embodiments, the plurality of rows of obstacles each extends at an angle of from about 1 degree to about 15 degrees, from about 3 degrees to about 12 degrees, from about 4 degrees to about 8 degrees, or from about 5 degrees to about 7 degrees relative to the average direction of fluid flow along said separation channel. In some embodiments, the plurality of rows of obstacles each extends at an angle of about 6 degrees relative to the average direction of fluid flow along said separation channel. In some embodiments, the plurality of rows of obstacles each extends at an angle of about 3 degrees, 4 degrees, 5 degrees, 6 degrees, 7 degrees, 8 degrees, 9 degrees, or 10 degrees relative to the average direction of fluid flow along said separation channel. In some embodiments, the plurality of rows of obstacles comprises a gap between adjacent rows of from about 8 μm to about 15 μm.

In some embodiments, the array of obstacles comprises a plurality of columns of obstacles. In some embodiments, the plurality of columns of obstacles comprise a gap between adjacent columns of from about 8 μm to about 15 μm.

In some embodiments, the microfluidic device further comprises a mixing channel disposed between and in fluidic communication with the separation channel and the one or more capture areas. In some embodiments, the mixing channel is serpentine-shaped.

In some embodiments, the microfluidic device further comprises a disbursement channel disposed between and in fluidic communication with the mixing channel and the one or more capture areas. In some embodiments, the disbursement channel comprises a branched network of channels extending from the mixing channel into two or more channels comprising said one or more capture areas.

In some embodiments, the microfluidic device further comprise a buffer inlet disposed adjacent to said sample inlet and in fluidic communication with said separation channel.

In some embodiments, the one or more capture areas are disposed at bends along a serpentine-shaped cell isolation channel of said microfluidic device. In some embodiments, the one or more capture areas are disposed at bends along a plurality of serpentine-shaped cell isolation channels of said microfluidic device.

In some embodiments, the separation channel flows into two distinct flowpaths, each comprising a mixing channel, a distribution channel, and said one or more capture areas. In some embodiments, the critical size is a diameter from 2 to 6 μm.

In some embodiments, the trap region of said capture channel comprises a width of about 12 μm, of from 10 to 14 μm, or from 8 to 16 μm. In some embodiments, the outflow region of said capture channel comprises a width of equal to or less than about 4 μm, 3.5 μm, 3 μm, 2.5 μm, or 2 μm. In some embodiments, the outflow region of said capture channel comprises a length of about 8-15 μm.

In some embodiments, the microfluidic device further comprises a sensor for detecting a signal from said trap region of said capture channel. In some embodiments, the signal is an optical signal or an electrical signal.

In some embodiments, the microfluidic, device further comprises a cell prefocusing, region adapted to disperse particles in a fluid flowing through said microfluidic device having a size at or above a critical size in a differential manner deviating from the direction of fluid flow towards said one or more capture channels.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

FIG. 8, panel B shows a fluorescence image of mixed Jurkat cells (stained green) and GBM U87 cells (stained blue), according to embodiments of the present invention.

FIG. 8, panel C shows an image of the cell supernatant after isolation of the barcoded NP-Mart-1. MILE tetramer from the Jurkat (green cells) and GBM U876 (blue cells) cell mixture of FIG. 8, panel B, according to embodiments of the present invention.

FIG. 8, panel D shows an image of the cells associated with the magnetic pulldown of the barcoded NP-Mart-1 MHC tetramer from the Jurkat (green cells) and GBM U876 (blue cells) cell mixture of FIG. 8, panel B, according to embodiments of the present invention.

DETAILED DESCRIPTION

Figure 1A:
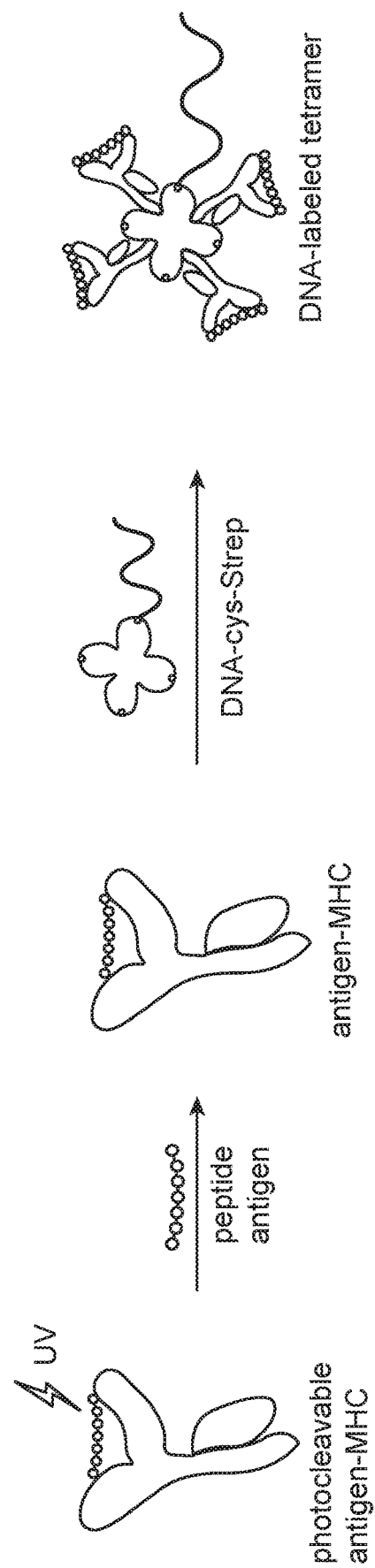
FIG. 1A is a schematic showing construction of a conditional antigen MHC molecule for loading different candidate antigen peptides using DNA-labeled and cysteine-modified streptavidin bound by four biotin-MHC molecules to form a library of DNA-labeled antigen-MHC complexes, as used in some embodiments of the present invention.

The details of various embodiments of the invention are set forth in the description below. Other features, objects, and advantages of the invention will be apparent from the description and the drawings, and from the claims.

Definitions

As used herein, "antigen-specific T cells" refer to cells that are distinguished from one another by their T cell receptors (TCRs), which give them their antigen specificity.

Embodiments of the present invention include a recombinant antigen-MHC complex that is capable of pairing with cognate T cells. As used herein, "antigen complex," "antigen-MHC," "antigen-MHC complex," "recombinant antigen-MHC complex," "peptide MHC," and "p/MHC," are used interchangeably to refer to a recombinant major histocompatibility complex with a peptide in the antigen binding groove. As used herein, "antigen" includes any antigen including patient-specific neoantigens.

As used herein with respect to the barcoded nanoparticle antigen-MHC complex, "a paired T cell" and "a T cell paired antigen MHC complex" refers to the complex of a T cell having a T cell receptor epitope that binds to an antigen peptide in a barcoded nanoparticle antigen-MHC complex.

As used herein, a "distinguishable fluorescent dye," and "distinguishable dye" refer to a dye of a color that is visually distinct from another dye.

The terms "DLD array" and "obstacle array" are used synonymously herein and can describe an ordered array of obstacles that are disposed in a flow channel through which a particle-bearing fluid can be passed.

In a DLD array, "fluid flow" and "bulk fluid flow" can be used synonymously to refer to the macroscopic movement of fluid in a general direction across an obstacle array. These terms do not take into account the temporary displacements of fluid streams for fluid to move around an obstacle in order for the fluid to continue to move in the general direction.

"The direction of bulk fluid flow" in an obstacle array device can refer to the average (e.g., macroscopic) direction of fluid flow through the device (i.e., ignoring local flow deviations necessitated by flow around obstacles in the fluid channel).

In a DLD array, the tilt angle θ can be the angle between the direction of bulk fluid flow and the direction defined by alignment of rows of sequential (in the direction of bulk fluid flow) obstacles in the array.

A "critical size" or "predetermined size" of particles passing through a DID array can be a parameter that describes the size limit of particles that are able to follow the laminar flow of fluid nearest one side of a gap through which the particles are travelling when flow of that fluid diverges from the majority of fluid flow through the gap. Particles larger than the critical size can be 'bumped' from the flow path of the fluid nearest that side of the gap into the flow path of the majority of the fluid flowing through the gap. In a DLD array, such a particle can be displaced by the distance of (the size of one obstacle+the size of the gap between obstacles) upon passing through the gap and encountering the downstream column of obstacles, while particles having sizes lower than the critical size (or predetermined size) will not necessarily be so displaced. When a profile of fluid flow through a gap is symmetrical about the plane that bisects the gap in the direction of bulk fluid flow, the critical size can be identical for both sides of the gap; however when the profile is asymmetrical, the critical sizes of the two sides of the gap can differ. When assessing a non-spherical particle, its size can be considered to be the spherical exclusion volume swept out by rotation of the particle about a center of gravity in a fluid, at least for particles moving rapidly in solution. The size characteristics of non-spherical particles can be determined empirically using a variety of known methods, and such determinations can be used in selecting or designing appropriate obstacle arrays for use as described herein. Calculation, measurement, and estimation of exclusion volumes for particles of all sorts are well known.

The Figures and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures.

Introduction

T-cell mediated immunity is characterized by the activation of antigen-specific cytotoxic T cells that are able to induce apoptosis in cells that display epitopes of foreign antigen in a major histocompatibility complex (MHC) on their surface. These cells displaying an MHC complex loaded with foreign antigen include virus-infected cells, cells with intracellular bacteria, and cancer cells displaying tumor antigens.

In order to utilize the T-cell mediated immunity process, e.g., for patient-specific cancer immunotherapy, one of the initial steps includes identification of the patients tumor-specific antigens neoantigens). For identification of a patient's putative neoantigens (tumor or pathogen), in silico predictive algorithmic programs are utilized that analyze the tumor, viral, or bacterial sequencing data to identify somatic mutations corresponding to putatively expressed neoantigens. Additionally, human leukocyte antigen (HLA) typing is determined from a tumor or blood sample of the patient, and this HLA information is utilized together with the identified putative neoantigen peptide sequences in a predictive algorithm for MHC binding, as verified by Fritsch et al, 2014, *Cancer Immunal Res.,* 2:522-529, the entire contents of which are herein incorporated by reference. These in silico analyses result in a ranked list of the patient's candidate neoantigen peptides which can be readily synthesized for screening of cognate antigen-specific T cells.

Embodiments of the present invention use recombinant antigen-loaded MHC compositions and facile decoding methods for high fidelity, rapid, and non-destructive isolation and identification of patient-specific T cell populations targeted to patient-specific antigens, e.g., neoantigens. Embodiments of the present invention use a nanoparticle (NP) having a unique polynucleotide barcode linked to a unique recombinant antigen-MHC complex. Utilizing the barcoded nanoparticle-antigen-MHC complex, T cells that pair with the antigen-MHC complex are then isolated in this antigen-MHC-T cell complex by selective isolation of the nanoparticle. This results in a population that has a small number of nanoparticles with a T cell paired antigen MHC complex (i.e., bound nanoparticles), and a large number of nanoparticles that have an antigen MHC complex that is not bound to a T cell (i.e., unbound nanoparticles). The bound nanoparticles must be efficiently separated from the unbound nanoparticles to isolate and analyze the appropriate barcodes.

In some embodiments, methods and devices are provided herein to separate bound and unbound nanoparticles, and to isolate bound nanoparticles to facilitate analysis and subsequent post-analysis processing.

In some embodiments provided herein is a microfluidic device that facilitates separation of bound and unbound nanoparticles and isolation of bound nanoparticles for analysis. In some embodiments, separation of bound and unbound nanoparticles is achieved in a microfluidic channel based upon deterministic lateral displacement (DLD), a size-based particle separation technique that relies on selective displacement of particles by an array of obstacles disposed in a flowing fluid. In some embodiments, isolation of the bound nanoparticles (i.e., barcoded T cells) is performed in microfluidic channels designed to isolate the barcoded T cells into individual single cell traps, where they can be further analyzed.

In some embodiments, the unique barcode for each isolated NP is identified by in situ amplification or using fluorescently labeled barcode sense strand "readers". Using this nanoparticle isolation and barcode identification methodology, the individual antigen-MHC-T cell complex is identified, but is not destroyed. Accordingly, the isolated T cell is available after identification as a valuable source for further characterization (e.g., tumor biomarker analysis) or for further propagation. Further growth of the T cell results in an enriched population of patient-derived T cells targeted to the patient-specific antigens. This population of patient-derived T cells targeted to the patient-specific antigens may be used for adoptive cell transfer into the patient as a means of immunotherapy targeting the tumor or pathogen.

The devices and methods described herein can be used, for example to identify neoantigen-specific T cell populations from the tumor infiltrating lymphocytes (TILs) or peripheral blood mononuclear cells (PBMCs) of a cancer patient. In some embodiments, the analysis of such T cells informs the construction of personalized cancer vaccines, or T cell receptor (TCR)-engineered T cell immunotherapies.

NP-Barcoded NACS Library Formation

Figure 1B:
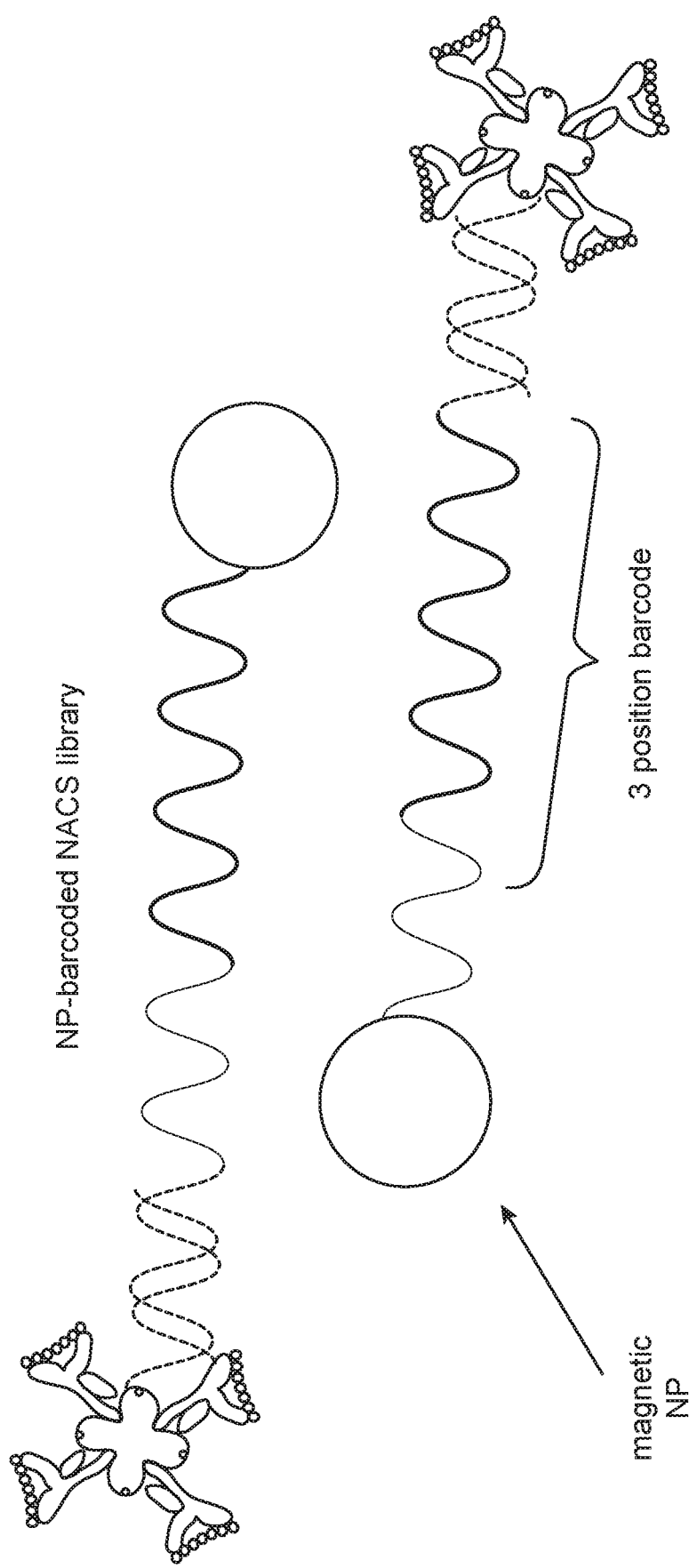
FIG. 1B is a schematic showing an example of a 3-position coding region barcode, as used in some embodiments of the present invention.

Compositions according to embodiments of the present invention include a recombinant antigen-MHC complexed with a barcoded nanoparticle (NP) sorting agent to form a barcoded NP-antigen-MHC complex. Formation of an antigen-specific MHC tetramer bound to a DNA linker (i.e., an antigen-MHC complex) to be linked with a nanoparticle is schematically shown in FIG. 1A. The barcoded NP-antigen-MHC complex is modular in form as schematically shown in FIG. 1B. The barcoded NP-antigen-MHC complex is made of an antigen-MHC complex (FIG. 1A) and a barcoded NP complex linked together by polynucleotide hybridization domains. The barcode comprises a coding region to identify the identity of the antigen in the antigen-MHC complex.

The components of the NP-barcoded NACS library are not shown to scale. The nanoparticle itself is much larger than the DNA-labeled tetramers, so that each nanoparticle can have up to $10^5$ identical barcoded NP-antigen-MHC complexes attached. This complex can also be referred to as a nanoparticle sorting agent, methods of using the complex can be referred to as nanoparticle-barcoded nucleic acid cell sorting (NP-barcoded NACS), and a collection of complexes can be referred to as an NP-barcoded NACS library. Each library element is prepared separately, and designed so that each peptide antigen is associated with a unique DNA barcode.

NP-barcoded MACS is a parallel method for searching through a heterogeneous mixture of lymphocytes for a defined group of antigen-specific T cell populations, which are then separated from the mixture. Once separated, the invention allows for the antigen-specificity of each individual T cell to be assigned by reading out the information contained within a molecular barcode. The cells may then be further analyzed.

Additional description of capture agents and related methods and systems for detecting and/or sorting antigen-specific T cells is found in U.S. Pat. No. 8,394,590 and US Publication No. 2017/0003288, each of which are incorporated by reference herein in its entirety. Specifically, U.S. Pat. No. 8,394,590 describes the construction of a library of DNA-labeled antigen-major histocompatibility complex (MHC) tetramers, and US 2017/0003288 describes coupling of the DNA-labeled tetramers to DNA-functionalized magnetic nanoparticles to prepare the NP-barcoded NACS library. Each of the modular components of the barcoded NP-antigen-MHC complex is described in more detail below.

NP-Antigen-MHC Complex

Each antigen, from the NP-barcoded NACS library, can potentially be recognized by, and thus bind to, a specific population of T cells, by interacting with the T cell receptor. The antigen is prepared so that it can be recognized by the T cell receptor that defines the T cell population of interest. It is also prepared so that it is attached to a magnetic nanoparticle (NP). In this way, once the antigen-specific T cells binds to the antigen, those T cells can be separated from the mixture using a magnet. In some embodiments, computational analysis of a cancer patient's tumor genome can be used to define a series of candidate neoantigens used to build the NP-barcoded NACS library. Additional description of methods to identify neoantigens can be found in US Publication No. 2017/0003288.

A recombinant antigen-MHC complex according to embodiments of the present invention includes a recombinant MHC molecule. In some embodiments of the present invention, the MHC complex may be an MHC Class I (MHC I) complex that pairs with CD8-positive (CD8+) T "killer" cells. In other embodiments of the present invention, the MHC complex may be an MHC Class II (MHC II) complex that pairs with CD4+"helper" T cells. In some embodiments of the present invention, the recombinant MHC molecule is an MHC Class II molecule expressed and loaded with a candidate antigen peptide as described in Novak et al., 1999, *J. Clin. Invest.* 104:R63-R67, the entire contents of which are herein incorporated by reference. Additional description of types of MHC molecules that can be used with the present invention can be found in US Publication No. 2017/0003288.

In some embodiments of the present invention, the recombinant MHC molecule is an MHC Class I molecule expressed as a conditional ligand. As the MHC class I molecule is unstable in the absence of peptide (i.e. antigen peptide), a recombinant MHC Class I molecule is expressed with a peptide having a cleavable moiety, that upon irradiation with UV light dissociates from the complex and disintegrates. However, if the UV disintegration of the cleavable peptide is performed in the presence of a "rescue peptide," the rescue peptide will readily replace the UV irradiated peptide in the binding groove, as described in Toebes et al., 2006. *Nat. Med.* 12:246-251 and Bakker et al., *PNAS*, 2008, 105:3825-3830, the entire contents of both of which are herein incorporated by reference. Using this technology, several assembled MHC Class I molecules can be easily loaded with candidate neoantigens to form a MHC class I neoantigen library for screening T cells.

In some embodiments of the present invention, the recombinant MHC molecule is a tetramer complex of four MHC molecules each loaded with the same candidate antigen peptide. Since most neoantigens have low binding affinities ($K_d$) for MHC proteins (e.g., 500 nM or lower) a tetrameric MHC complex allows for increased binding avidity, thereby increasing the sensitivity of this antigen-MHC tetrameric probe for pairing with low abundant cognate T cells.

In some embodiments of the present invention, an MHC tetramer is formed using modified streptavidin conjugated with four biotin-modified MHC molecules. The streptavidin is modified to enable binding of a polynucleotide (e.g., DNA or RNA) linker. Modification of the streptavidin includes a binding moiety that can pair with (e.g., covalently bind to) a corresponding cognate binding moiety linked to the polynucleotide molecule. Any suitable pair of binding moieties may be used to modify streptavidin and the polynucleotide for linkage. Non-limiting examples of binding moiety pairs include a thiol group (e.g., cysteine) and maleimide, adamantane and cyclodextrin, an amino group and a carboxy group, and an azido group and alkynl group (i.e., click chemistry). An example of a cysteine-modified streptavidin linked to a maleimide-modified DNA hybridization domain (the "DNA-labeled tetramer") is shown in FIG. 1A.

According to embodiments of the present invention, a polynucleotide hybridization domain is linked to the 3' end of the polynucleotide detection tag of the barcoded NP, and a second polynucleotide hybridization domain is linked to the streptavidin scaffold of the antigen-MHC complex. Accordingly, the antigen-MHC complex is linked to a barcoded nanoparticle through hybridization of complementary hybridization domains. In some embodiments of the present invention, the first polynucleotide hybridization domain and the second polynucleotide hybridization domain may be single stranded. DNA (ssDNA) having a first and a second hybridization sequence, respectively, where the first and second hybridization sequences are complementary, resulting in a linker of hybridized double stranded DNA (dsDNA), shown as overlapping black lines in FIG. 1B.

Barcoding

Embodiments of the present invention include a modified nanoparticle linked to a polynucleotide detection tag (i.e., the barcode), where the polynucleotide detection tag includes at least one coding region. In some embodiments, the barcode is a polynucleotide detection tag made of coding regions that provide a unique antigen-specific sequence for identification after T cell isolation. Therefore, as is understood by a person having ordinary skill in the art, each unique antigen-MHC complex is linked (i.e., hybridized) to a unique barcode sequence.

In some embodiments of the present invention the polynucleotide sequences are ssDNA. In some embodiments of the present invention, the polynucleotide detection tag sequences are modified at their 5' end to a binding moiety for attachment to a nanoparticle. For example, the polynucleotide detection tag (ssDNA barcode) sequences are conjugated to a biotin molecule for binding to a streptavidin-nanoparticle; however any suitable binding moiety may be used.

As described herein and as understood by a person skilled in the art, suitable binding moiety pairs are known in the art. Non-limiting examples of binding moieties include thiol, maleimide, adamantane, cyclodextrin, amine, carboxy, azide, and alkyne.

With the barcoded coding region forming a polynucleotide detection tag, each antigen is associated with a unique n-position barcode polynucleotide sequence allowing for n possible sequences per position. An example of a 3-position barcode is shown as different colors (e.g., yellow, red, or green) in FIG. 1B. This 3-position barcode yields a $3^3$, or 27-plex antigen library with each of the 27 different antigens having a specific barcode that can be readily determined upon isolation of the complex. The ability to screen 27 different antigens with one T cell suspension is a significant advantage over the current more time consuming methods.

When a NP-barcoded NACS library element binds to a T cell, the magnetic nanoparticle is also attached to the T cell. Such a T cell is said to be 'barcoded.' All barcoded T cells can thus be separated from the other non-barcoded T cells using magnetic separation techniques.

Nanoparticles

In some embodiments, the nanoparticle is magnetic for isolation using a magnet. In some embodiments, the nanoparticle is a polystyrene particle isolated by gravity. According to embodiments of the present invention, the nanoparticle is modified with a binding moiety for linking to the polynucleotide coding region. Modification of the nanoparticle includes a binding moiety that can pair with (e.g., covalently bind to) a corresponding cognate binding moiety linked to the polynucleotide molecule. Any suitable pair of binding moieties may be used to modify the nanoparticle and the polynucleotide detection tag for linkage. Non-limiting examples of binding moiety pairs include a thiol group (e.g., cysteine) and maleimide, adamantane and cyclodextrin, an amino group and a carboxy group, and an azido group and alkynl group.

Purification of Antigen-Specific T Cells

Embodiments of the present invention include the use of a barcoded nanoparticle-antigen-MHC complex for screening antigen-specific T cells. As understood by a person skilled in the art, a single antigen may be assayed using the complex in the presence of T cells. However, assaying one candidate antigen is not as efficient as screening multiple candidate antigens.

According to some embodiments of the present invention, isolation and identification of patient-derived and antigen-specific T cells using a library of barcoded-NP-antigen-MHC complexes includes incubating the candidate antigen complexes with patient-derived T cells. In some embodiments, T cells are prepared using standard methods that start from a tissue such as blood, a lymph node, or a tumor.

In some embodiments, the patient-derived T cells are isolated from the patient's peripheral blood mononuclear cells (PBMCs) or tumor infiltrating lymphocytes (TILs). In some embodiments of the present invention, both CD4+ and CD8+ T cells are labeled and sorted from PBMCs or TILS using anti-CD4 and anti-CD8 fluorescent antibodies with live populations of CD4+ and CD8+ single-positive cells sorted using fluorescence-activated cell sorting (FACS), in order to isolate only CD4+ or CD8+ cells. In some embodiments of the present invention, T cells that are positive for both CD4 and CD8 may be isolated using an anti-CD3 fluorescent antibody followed by FACS. A person skilled in the art is able to determine the type of T cells to isolate for the type or types of antigen-MHC complex being used.

Embodiments of the present invention include incubating a barcoded NP-antigen-MHC complex library with a suspension of CD4+, CD8+ or CD4+/CD8+ T cells. Each library element is separately prepared (FIG. 1B), but then all library elements are combined and mixed with a single cell suspension of T cells.

Incubation of the nanoparticle library with the T cell suspension allows for a complete and thorough exposure of the nanoparticle-bound antigen to the various T-cell receptors. This method may include rocking or rotation of the cells.

Figure 1C:
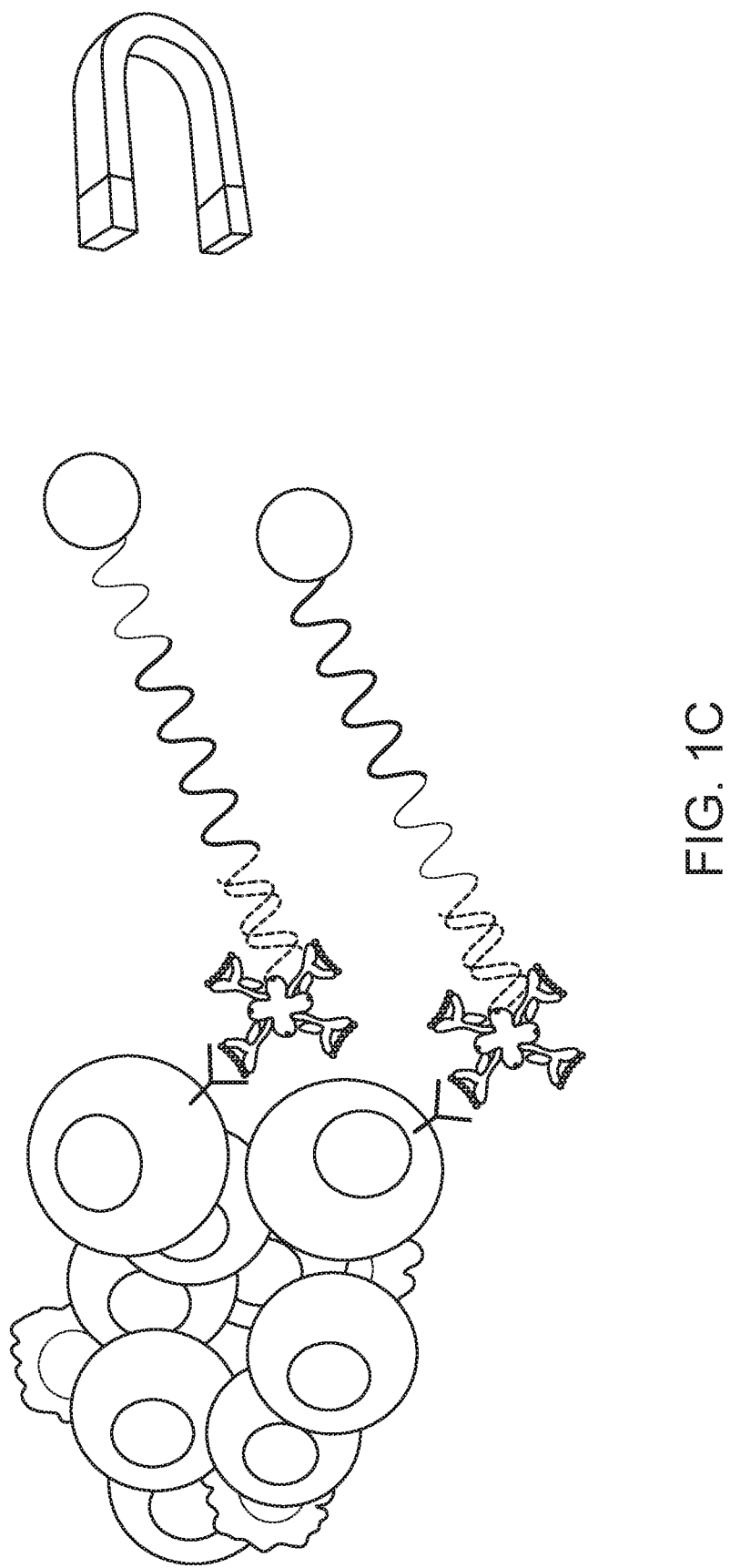
FIG. 1C is a schematic depicting a barcoded magnetic NP-antigen-MHC complex paired with a cognate T cell receptor (TCR) on a T cell, and isolation of the magnetic NP with a magnet, according to some embodiments of the present invention.

Following incubation of the antigen complex and the T cells, the nanoparticle is selectively isolated or selectively collected. Barcoded T cells will likely be bound to many identical copies of identical NP-barcoded NACS library elements, and can be separated based on these interactions. For example, if the nanoparticle is magnetic, applying a magnet to the suspension allows for separation of nanoparticles in a complex with antigen paired T cells and removal of unpaired T cells. An example of isolated magnetic nanoparticles with paired T cells is shown schematically in FIG. 1C. Alternatively, if the nanoparticle is a polystyrene nanoparticle, the unpaired T cells may be separated by gravity (e.g., centrifugation). After separation of unpaired T cells, in some embodiments, the isolated nanoparticles are washed at least once to remove any non-specifically associated T cells.

A full NP-barcoded NACS library may consist of 5-1000 different antigens, each with their own DNA barcode, although a 50-element library is typical. The magnetic nanoparticles used in the library are around 1 micrometer in diameter, and T cells can range from 8-20 micrometers in diameter. Each antigen-specific T cell will have many copies of an identical T cell receptor (TCR), so that an antigen-specific T cell can potentially be barcoded by many identical copies of a specific NP-barcoded NACS library element. The T cells will appear dark in color when barcoded, since the nanoparticles themselves are black.

For a sample of tumor infiltrating lymphocytes (TILs) or Peripheral Blood Mononuclear Cells (PBMCs) that contains $10^4$ CD8+ T cells, and for a (typical) NP-barcoded NACS library size of 50, often between 5 and 200 T cells will be barcoded by between 1 and 15 of the 50 library elements. Because the T cell receptor interaction with the antigens is highly specific, each individual barcoded T cell will only be associated with a single library element, although multiple copies of that library element can (and will likely) be attached to the T cell. Each barcoded T cell will thus be associated with between 1-400 nanoparticles. Approximately $10^8$ nanoparticles, representing the 50 NP-barcoded NACS library elements, might be mixed with the $10^4$ T cells in the barcoding process. Unbound NP-barcoded elements can outnumber the barcoded T cells by about $10^6:1$ or more.

Microfluidic Device for Separation and Isolation

After magnetic separation of barcoded T cells from unbounded T cells, the population comprising barcoded T cells will also include capture of barcoded nanoparticles that are not bound to T cells. When the barcoded nanoparticles have a plurality of distinct barcodes, this could generate many false positive signals unless the unbound nanoparticles are separated from the T cell bound nanoparticles. However, there are typically a vast number of unbound nanoparticles relative to the nanoparticles bound to the T cells. Therefore, in order to correctly read out the DNA barcodes on the barcoded T cells, or to do further analysis of those T cells, it is desirable to completely separate the barcoded T cells from the excess nanoparticles. This represents a challenging separation problem. Provided herein is a device and a high throughput method to separate bound and unbound nanoparticles (i.e., separating barcoded T cells from barcoded nanoparticles that are not bound to T cells).

Provided herein, according to some embodiments, is a microfluidic device that performs two key functions. First, the unattached nanoparticles are spatially separated from the barcoded T cells with a high fidelity (e.g., 100% fidelity). Second, the barcoded T cells are isolated into individual single cell traps for subsequent analysis. In some embodiments, the analysis assigns each individual captured cell to be assigned to a specific antigen, e.g., using methods as described in US Publication No. 2017/0003288, incorporated by reference in its entirety.

Deterministic Lateral Displacement (DLD) Array

In some embodiments, the microfluidic device uses the principle of deterministic lateral displacement (DLD) to separate, in a flowing solution of particles and solvent, particles according to the particle size. In other words, the invention takes advantage of the size difference of a T cell (10-20 micrometers diameter) relative to an unbound NP-barcoded MACS library element (1 micrometer). Once separated, the barcoded T cells are isolated into a series of cell traps that are part of the microfluidics design.

DLD arrays (also known as "obstacle array") devices have been described, and their basic operation is explained, for example in U.S. Pat. No. 7,150,812, which is incorporated herein by reference in its entirety. Referring to FIGS. 3 and 4 of U.S. Pat. No. 7,150,812, a DLD array can operate essentially by segregating particles passing through an array (generally, a periodically-ordered array) of obstacles, with segregation occurring between particles that follow an "array direction" that is offset from the direction of bulk fluid flow or from the direction of an applied field.

Figure 8:
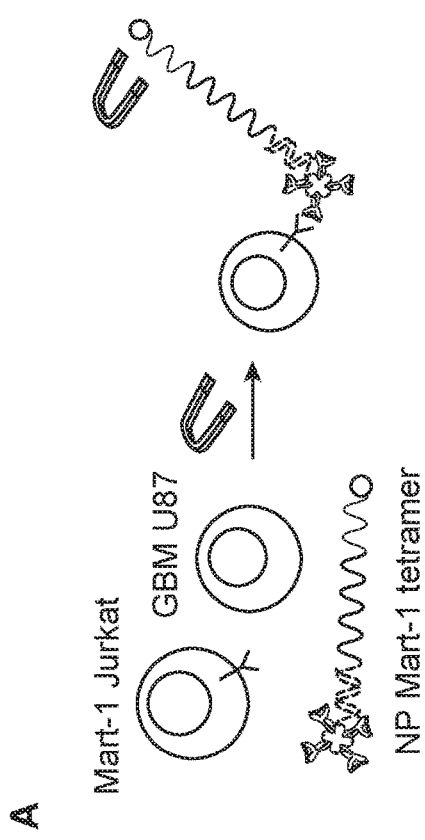
FIG. 8, panel A is a schematic illustration of a barcoded NP-Mart-1 MHC tetramer for capture of Jurkats cells transduced with a Mart-1 specific T-cell receptor (green cell) from a mix of Jurkat and GBM U876 cells (blue cell), according to embodiments of the present invention.
Figure 8:
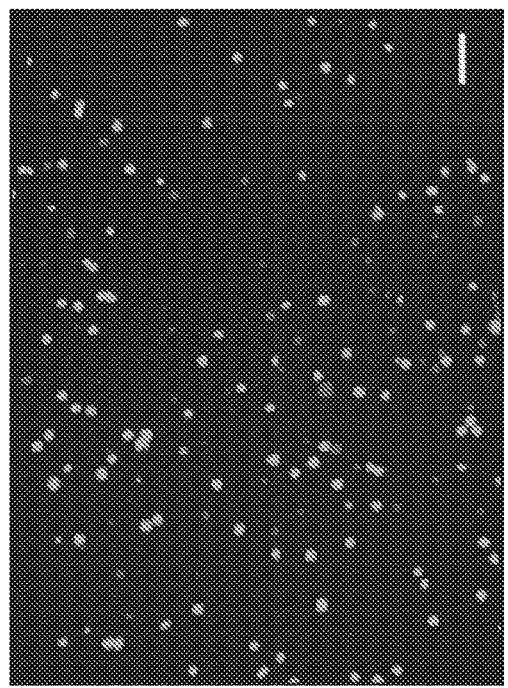
Figure 8:
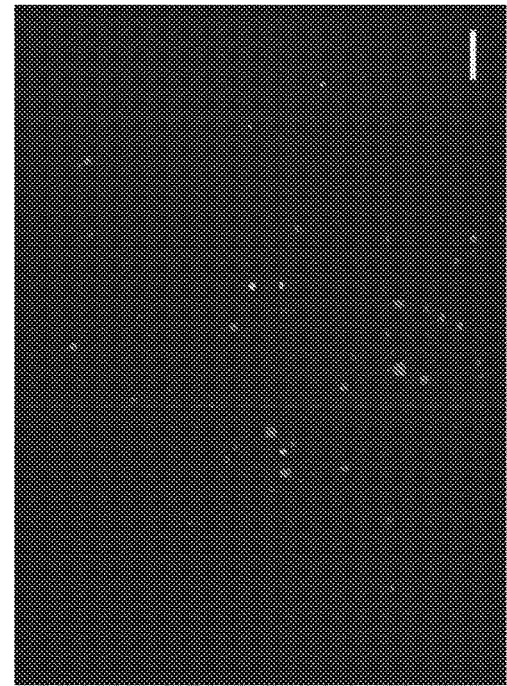
Figure 8:
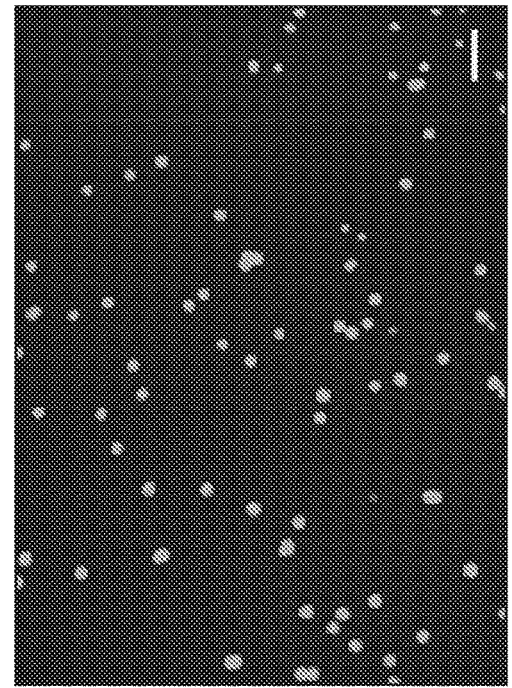

At the level of flow between two adjacent obstacles under conditions of relatively low Reynold's number, fluid flow can occur in a laminar fashion. Considering the volumetric flow between two obstacles in hypothetical layers (e.g., modeling the flow by considering multiple adjacent stream tubes of equal volumetric flow between the Obstacles, as shown in FIG. 8 of U.S. Pat. No. 7,150,812), the likelihood that fluid in a layer will pass on one side or the other of the next (i.e., downstream) obstacle can be calculable by standard methods (see, e.g., Inglis et al., 2006, Lab Chip 6:655-658). For an ordered array of obstacles offset from the direction of bulk fluid flow, the arrangement of the obstacles can define an array direction corresponding to the direction in which the majority of fluid layers between two obstacles travels. A minority of fluid layers can travel around the downstream obstacle in a direction other than the array direction.

The path that a particle passing between the two obstacles can take can depend on the flow of the fluid in the layers occupied by the particle. Conceptually, for a particle having a size equal to one of the hypothetical fluid layers described in the preceding paragraph, the particle can follow the path of the fluid layer in which it occurs, unless it diffuses to a different layer. For particles larger than a single fluid layer, the particle can take the path corresponding to the majority of the fluid layers acting upon it. Particles having a size greater than twice the sum of the thicknesses of the minority of layers that travel around a downstream obstacle in the direction other than the array direction can be acted upon by more fluid layers moving in the array direction, meaning that such particles will travel in the array direction. This concept is also illustrated in FIGS. 5-11 of U.S. Pat. No. 7,150,812. Thus, there can be a "critical size" for particles passing between two obstacles in such an array, such that particles having a size greater to that critical size can travel in the array direction, rather than in the direction of bulk fluid flow and particles having a size less than the critical size can travel in the direction of bulk fluid flow. Particles having a size precisely equal to the critical size can have an equal chance of flowing in either of the two directions. By operating such a device at a high Peclet number (i.e., such that advective particle transport by fluid layers greatly outweighs diffusive particle between layers), the effects of diffusion of particles between fluid layers can be ignored.

Devices for separating particles based on size and/or using DLD are described, e.g., in U.S. Pat. Nos. 7,150,812, 7,318,902, 7,472,794, 7,735,652, 7,988,840, 8,021,614, 8,282,799, 8,304,230, 8,579,117, and PCT Publication No. WO2012/094642, which are incorporated by reference herein in their entireties.

Described herein are devices comprising a DLD array that are useful for segregating particles by size. In one embodiment, a device includes a body defining a microfluidic flow channel for containing fluid flow. An array of obstacles is disposed within the flow channel, such that fluid flowing through the channel flows around the obstacles. The obstacles extend across the flow channel, generally being either fixed to, integral with, or abutting the surface of the flow channel at each end of the obstacle.

The obstacles can be arranged in rows and columns, in such a configuration that the rows define an array direction that differs from the direction of fluid flow in the flow channel by a tilt angle ($\theta$) that has a magnitude greater than zero. The maximum operable value of $\theta$ can be ½ radian. The value of $\epsilon$ can be preferably ⅕ radian or less, and a value of ⅒ radian has been found to be suitable in various embodiments of the arrays described herein. The obstacles that are in columns define gaps between themselves, and fluid flowing through the flow channel is able to pass between these gaps, in a direction that is generally transverse with respect to the columns (i.e., generally perpendicular to the long axis of the obstacles in the column and generally perpendicular to a plane extending through the obstacles in the column).

The obstacles can have shapes so that the surfaces (upstream of, downstream of, or bridging the gap, relative to the direction of bulk fluid flow) of two obstacles defining a gap are asymmetrically oriented about the plane that extends through the center of the gap and that is parallel to the direction of bulk fluid flow through the channel. That is, the portions of the two obstacles can cause asymmetric fluid flow through the gap. The result can be that the velocity profile of fluid flow through the gap is asymmetrically oriented about the plane. As a result of this, the critical particle size for particles passing through the gap adjacent to one of the obstacles can be different than the critical particle size for particles passing through the gap adjacent to the other of the obstacles.

The obstacles can be solid bodies that extend across the flow channel, in some cases from one face of the flow channel to an opposite face of the flow channel. Where an obstacle is integral with (or an extension of) one of the faces of the flow channel at one end of the obstacle, the other end of the obstacle can be sealed to or pressed against the opposite face of the flow channel. A small space (preferably too small to accommodate any of particles of interest for an intended use) can be tolerable between one end of an obstacle and a face of the flow channel, provided the space does not adversely affect the structural stability of the obstacle or the relevant flow properties of the device. In some embodiments described herein, obstacles are defined by a cross-sectional shape (e.g., round or triangular). Methods of imparting a shape to an obstacle formed from a monolithic material are well known (e.g., photolithography and various micromachining techniques) and substantially any such techniques may be used to fabricate the obstacles described herein. The sizes of the gaps, obstacles, and other features of the arrays described herein depend on the identity and size of the particles to be handled and separated in the device, as described elsewhere herein. Typical dimensions are on the order of micrometers or hundreds of nanometers, but larger and smaller dimensions are possible, subject to the limitations of fabrication techniques.

The obstacles can generally be organized into rows and columns (use of the terms rows and columns does not mean or imply that the rows and columns are perpendicular to one another). Obstacles that are generally aligned in a direction transverse to fluid flow in the flow channel can be referred to as obstacles in a column. Obstacles adjacent to one another in a column can define a gap through which fluid flows. Obstacles in adjacent columns can be offset from one another by a degree characterized by a tilt angle, designated $\theta$ (theta). Thus, for several columns adjacent to one another (i.e., several columns of obstacles that are passed consecutively by fluid flow in a single direction generally transverse to the columns), corresponding obstacles in the columns can be offset from one another such that the corresponding obstacles form a row of obstacles that extends at the angle $\epsilon$ relative to the direction of fluid flow past the columns. The tilt angle can be selected and the columns can be spaced apart from each other such that 1/θ (when θ is expressed in radians) is an integer, and the columns of obstacles repeat periodically. The obstacles in a single column can also be offset from one another by the same or a different tilt angle. By way of example, the rows and columns can be arranged at an angle of 90 degrees with respect to one another, with both the rows and the columns tilted, relative to the direction of bulk fluid flow through the flow channel, at the same angle of θ.

Microfluidic Devices for Separation of Unbound Nanoparticles and Barcoded T Cells In some embodiments, provided herein is a microfluidic device comprising a separation channel. The separation channel comprises an array of obstacles adapted to disperse particles having a size at or above a critical size in a differential manner deviating from the average flow direction in a flow of a heterogeneous fluid sample through the separation channel.

The array of obstacles are based on the principles of deterministic lateral displacement, and are designed to offer continuous separation, focusing, and isolation of the barcoded T-cells for the analysis of neoantigen-specific CD8+ T cells. Firstly, the engineered obstacle array is situated in the device in order to separate the barcoded T-cells (large particles) from the mixture of such T-cells and unattached small nanoparticles based on the size differential. In some embodiments, this obstacle array comprises a plurality of columns of obstacles and a plurality of rows of obstacles. In some embodiments, the plurality of rows of columns extend at an angle relative to the average flow direction of said separation channel. In some embodiments, the plurality of rows of columns extend at an angle relative to the average flow direction In some embodiments, the plurality of rows of columns extend at an angle relative to the average flow direction through the separation channel of from about 1 degree to about 15 degrees, from about 3 degrees to about 12 degrees, from about 4 degrees to about 8 degrees, or from about 5 degrees to about 7 degrees.

In some embodiments, the plurality of rows of columns extend at an angle relative to the average flow direction through the separation channel of about 6 degrees.

In some embodiments, the plurality of rows of columns extend at an angle relative to the average flow direction through the separation channel of about 3 degrees, 4 degrees, 5 degrees, 6 degrees, 7 degrees, 8 degrees, 9 degrees, or 10 degrees.

In some embodiments, the rows of obstacles comprises a gap between adjacent rows of from about 8 µm to about 15 µm. In some embodiments, the plurality of columns of obstacles comprise a gap between adjacent columns of from about 8 µm to about 15 µm.

After flowing through the separation channel, in some embodiments, the separated cells continuously flow along one wall of the microfluidic channel from the separation channel and plurality of obstacles acting as a DLD array in a cell prefocusing area. The cell prefocusing area directs cells towards capture channels to trap individual cells with high-efficiency single cell isolation.

Lastly, cells are individually captured in an array of cell capture channels comprising a trap area and a buffer flow area. The trap area collects an individual cell from the flow through the device, and the outflow area allows sample fluid to pass through the capture channel, but prevents a cell from passing through. Once the cell is successfully captured at the single cell level, then subsequent analysis of a barcode paired with the cell, can be carried out on a chip. In some embodiments, this includes screening of neoantigen-specific CD8+ T cells. In some embodiments, analysis of the barcode paired with a trapped cell can be used to identify an antigen-specificity of the isolated cell. In some embodiments, analysis of the barcode paired with a trapped cell can be used to identify a neoantigen in a subject. In some embodiments, analysis of the barcode paired with a trapped cell can be used to identify a T-cell receptor in a subject. In some embodiments, analysis of the barcode paired with a trapped cell can be used to characterize T cell populations in a subject.

Provided below are exemplary embodiments of microfluidic devices of the present invention, which can be used to separate barcoded T cells from unbound nanoparticles, and for trapping an individual T cell for subsequent analysis or processing of a viable trapped T cell.

Figure 2A:
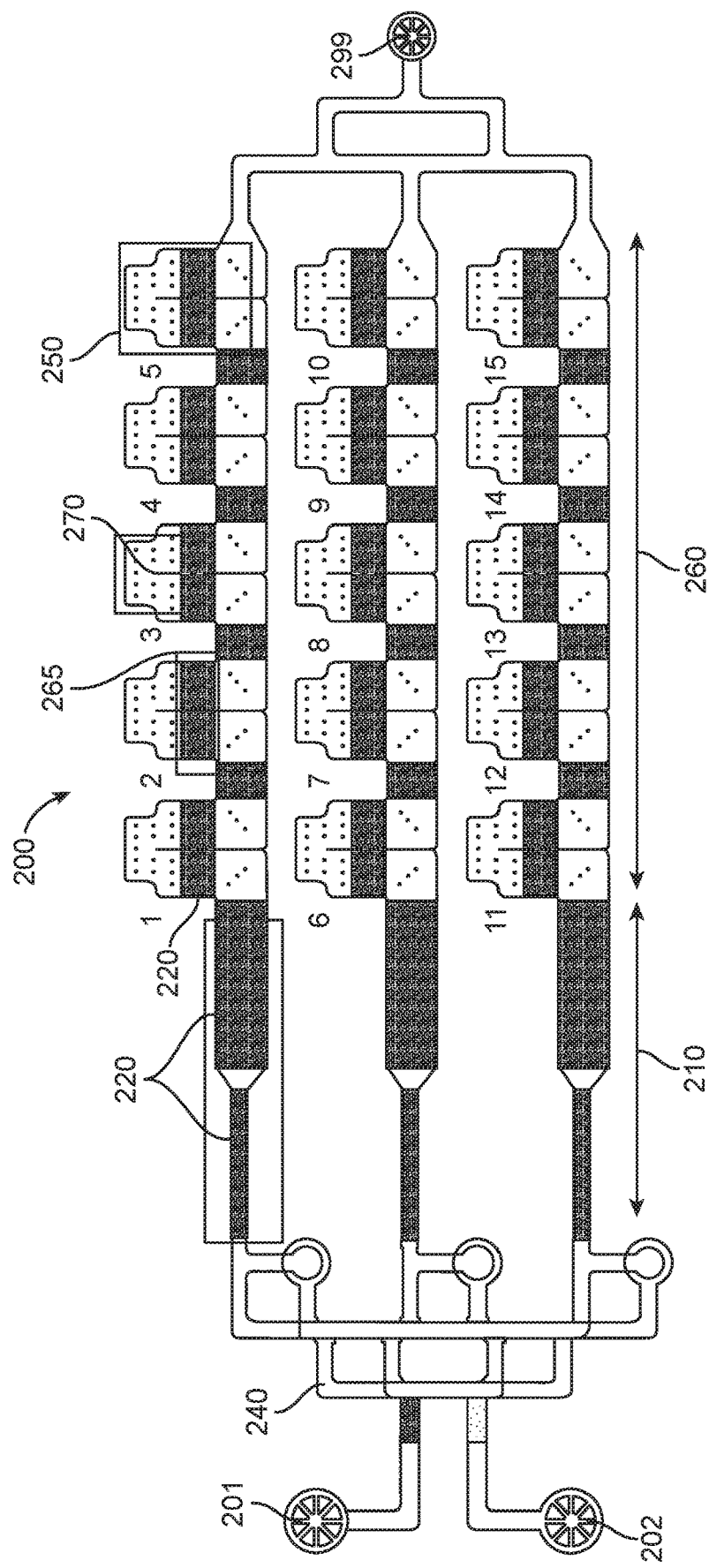
FIG. 2A is a cross-sectional representation of one embodiment of a microfluidic device, according to an embodiment of the invention.

FIG. 2A is a cross-sectional view of a design of a microfluidic device 200 for the separation of barcoded T cells from unattached nanoparticles, according to an embodiment of the invention. As shown, the microfluidic device comprises a sample inlet port 201 and a buffer inlet port 202, an outlet port 299 to remove waste from the chip. The microfluidic device comprises a separation channel 210 that includes DLD arrays 220 arrays of obstacles) for the separation of large barcoded cells from unbound nanoparticles. The microfluidic device further comprises a cell isolation channel 260 comprising a plurality of capture areas 250 comprising a cell prefocusing area 265 comprising a DLD array 220 and a linear arrays of capture channels 270. The cell prefocusing area 265 pushes or maintains barcoded cells along a wall of the microfluidic device adjacent to the linear array of capture channels 270. The capture channels are configured to trap single barcoded T cells for subsequent analysis.

In order to separate the barcoded T-cells in a buffer solution while leaving the unattached nanoparticles in a sample solution, a DLD array has been designed with an array of obstacles arranged and shaped to efficiently separate barcoded T cells from unbound nanoparticles. Previous papers report that circular pillars are prone to clogging within the gap between the pillars resulting in a drastic reduction in separation efficiency. To resolve this issue, topology optimization has been applied to find optimal structure which would increase the gap between the pillars without scarifying the critical diameter. It has been shown that this new pillar shape allows the gap between the pillars to be increased by 30% compared to the circular pillar shape.

Figure 2B:
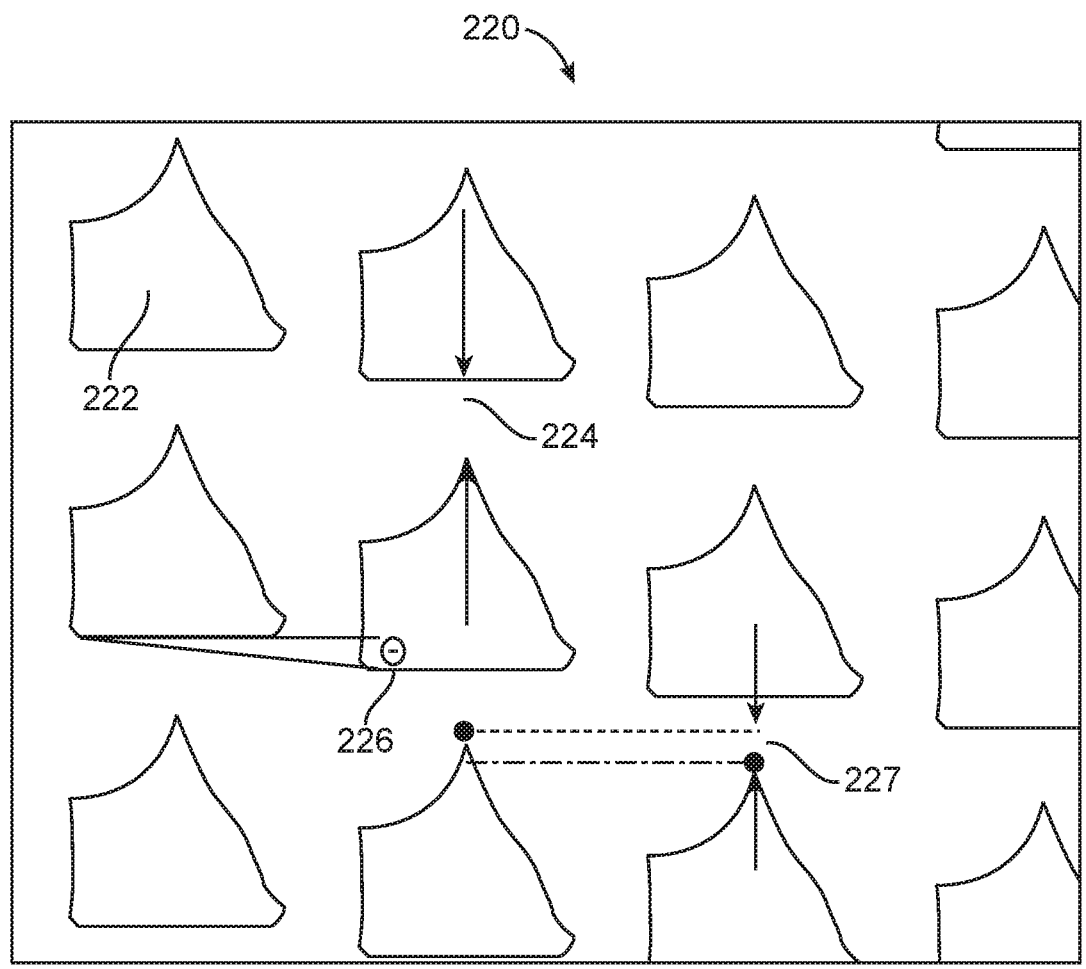
FIG. 2B is a cross-sectional representation of obstacles in a DM separation channel of the microfluidic device, according to an embodiment of the invention.

An embodiment of an array of obstacles to use in a microfluidic device as a DLD array to separate unbound nanoparticles and barcoded T cells is illustrated in FIG. 2B. The parameters of the array and the obstacle topology 222 have been optimized to separate T-cells, which are bigger than 4 µm, from unbound nanoparticles smaller than 4 µm. As shown in FIG. 2B, obstacles are arranged in rows and columns, and the rows are offset from an average direction of fluid flow in the channel by a tilted angle 226. In some embodiments, the tilted angle 226 is about 6 degrees. The DUD array is also characterized by a gap 224 between adjacent obstacles along a column. In some embodiments, this gap 224 is about 13 µm. The DLD array is also characterized by row shift 227 between adjacent obstacles on a row, which is related to the tilted angle. In some embodiments, the row shirt 227 is about 5 µm.

Figure 2C:
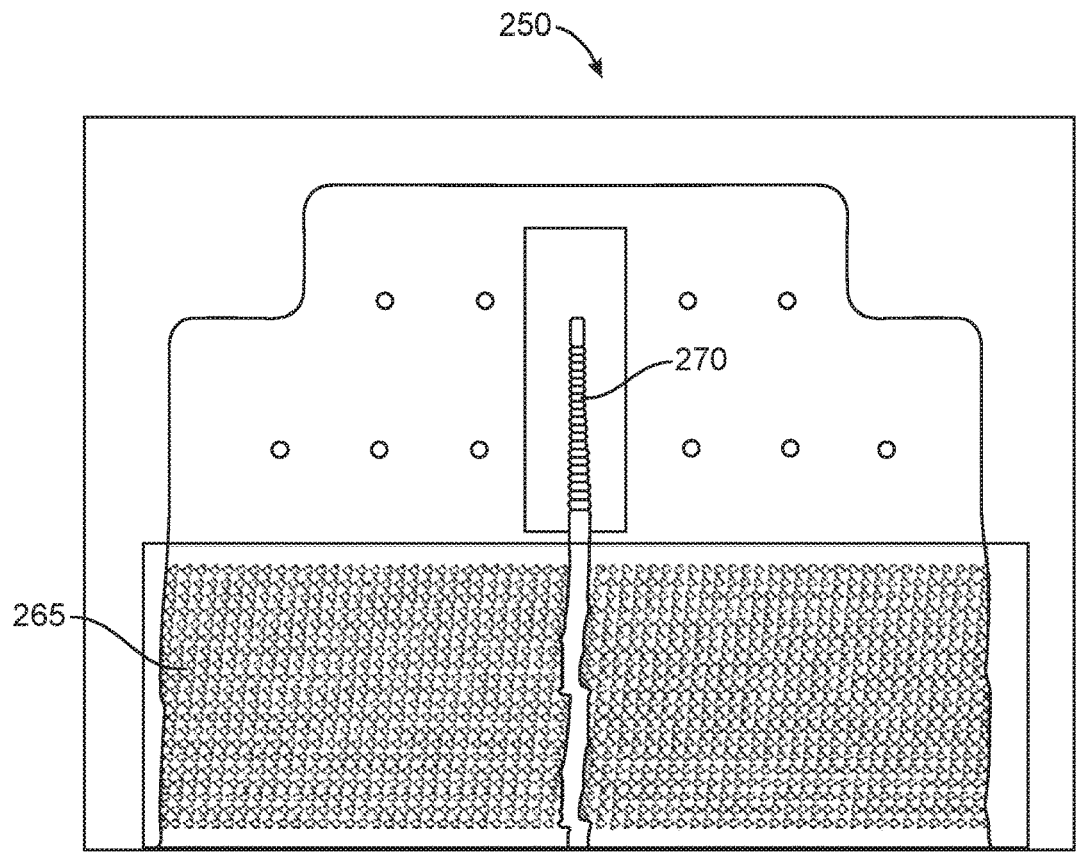
FIG. 2C is a cross-sectional representation of a cell isolation channel and a linear array of capture channels of the microfluidic device, according to an embodiment of the invention.
Figure 2D:
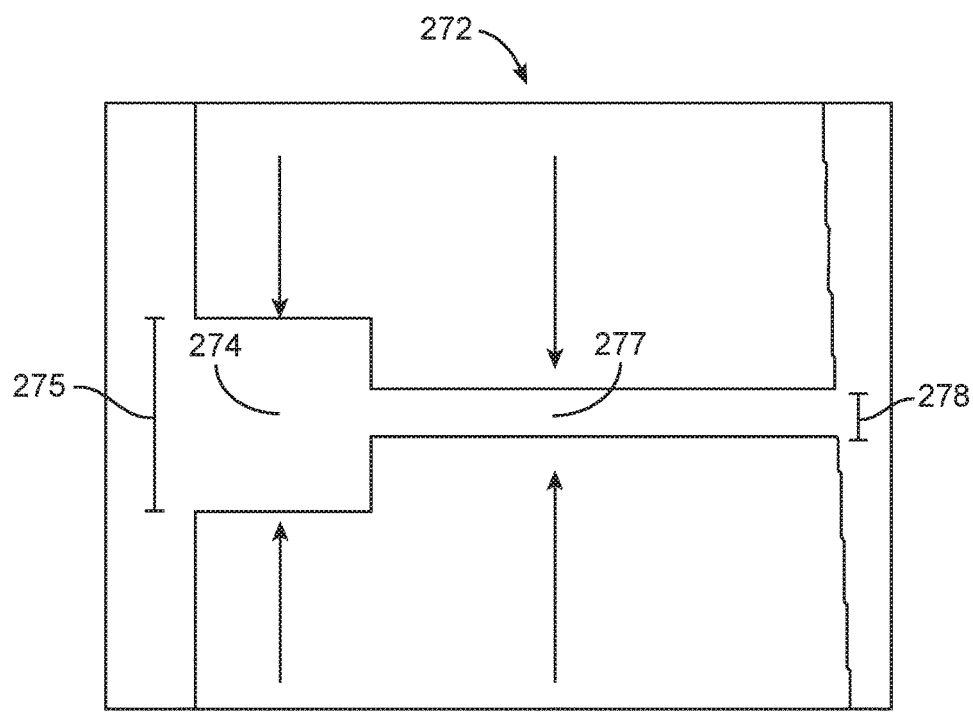
FIG. 2D is a cross-sectional representation of a capture channel including a trap region and a buffer outflow region.

After separation of the barcoded T-cell from unbound nanoparticles in the separation channel 220, it is essential to capture the single cell at the designated point at high efficiency since the separated neoantigen-specific CD8+ T cells are rare in patient sample. In order to realize this function, the cells, which are previously separated by DLD arrays, are allowed to flow along one wall of the microfluidic channel through the cell focusing area 265 to focus them near the channel wall. Simultaneously, the focused cells are forced into a capture channel 272 in a linear array of capture channels 270 (FIG. 2C and FIG. 2D). A single barcoded T-cell flows into the trap region 274 of the capture channel 272 and is sterically hindered from translocating through the capture channel due to the buffer outflow region 277 of the capture channel 272, which has a width 278 that is too small to allow passage of the cell through the capture channel 272. In some embodiments, the width of the buffer outflow region of the capture channel 278 is about 3 µm. In some embodiments, the width of the trap region of the capture channel 275 is about 12 µm to facilitate single molecule capture and trapping.

As shown in FIG. 2C, twenty single trap regions 274 are set in a linear array of capture channels 270 for each capture area 250. FIG. 2A shows an embodiment of the microfluidic device 200 with fifteen total capture areas 250.

Figure 2E:
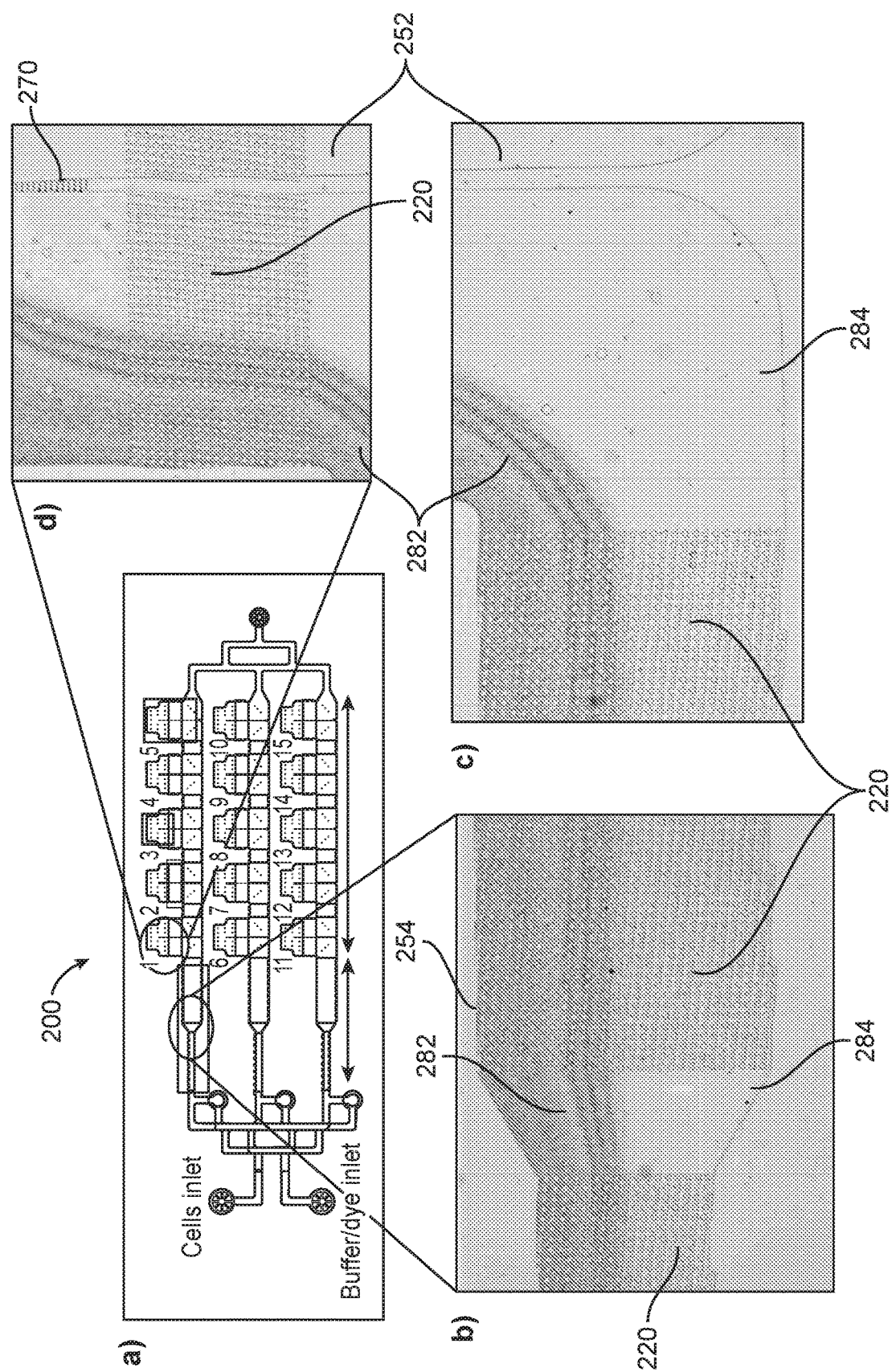
FIG. 2E is a cross-sectional representation of the embodiment of a microfluidic device as shown in FIG. 2A, and also including optical micrographs of selected sections of the microfluidic device with sample flowing through, showing effective separation of bound nanoparticles (i.e., barcoded T cells) and unbound nanoparticles.

FIG. 2E, panel (a), shows a cross-sectional view of a design of the DLD microfluidic device 200 for the separation of barcoded T cells 284 from unattached nanoparticles 282, according to an embodiment of the invention. Images of the microfluidic device in use during separation and isolation are shown FIG. 2E for different segments of the device, including (b) a section of a separation channel, (c) an end of a separation channel, and (d) a cell capture area 250 comprising a cell focusing section 250 with a DLD array 220 leading into an array of cell traps 270. The microfluidic device 200 comprises three microchannels through which the solution of barcoded T cells and nanoparticles are flowed. Each microchannel has regions of posts 220 (i.e., obstacles) that are the primary filters for spatially separating the unbound nanoparticles 282 from the barcoded. T cells 284. The barcoded T cells 284 are separated to flow along one wall of the microchannel 252, while the unattached nanoparticles flow along the other wall 254. At specific locations, a linear array of cell traps 270 is incorporated to capture and hold in place isolated single barcoded T cells, while the unbound nanoparticles 282 flow through the device and are delivered to a waste outlet 299.

Figure 3A:
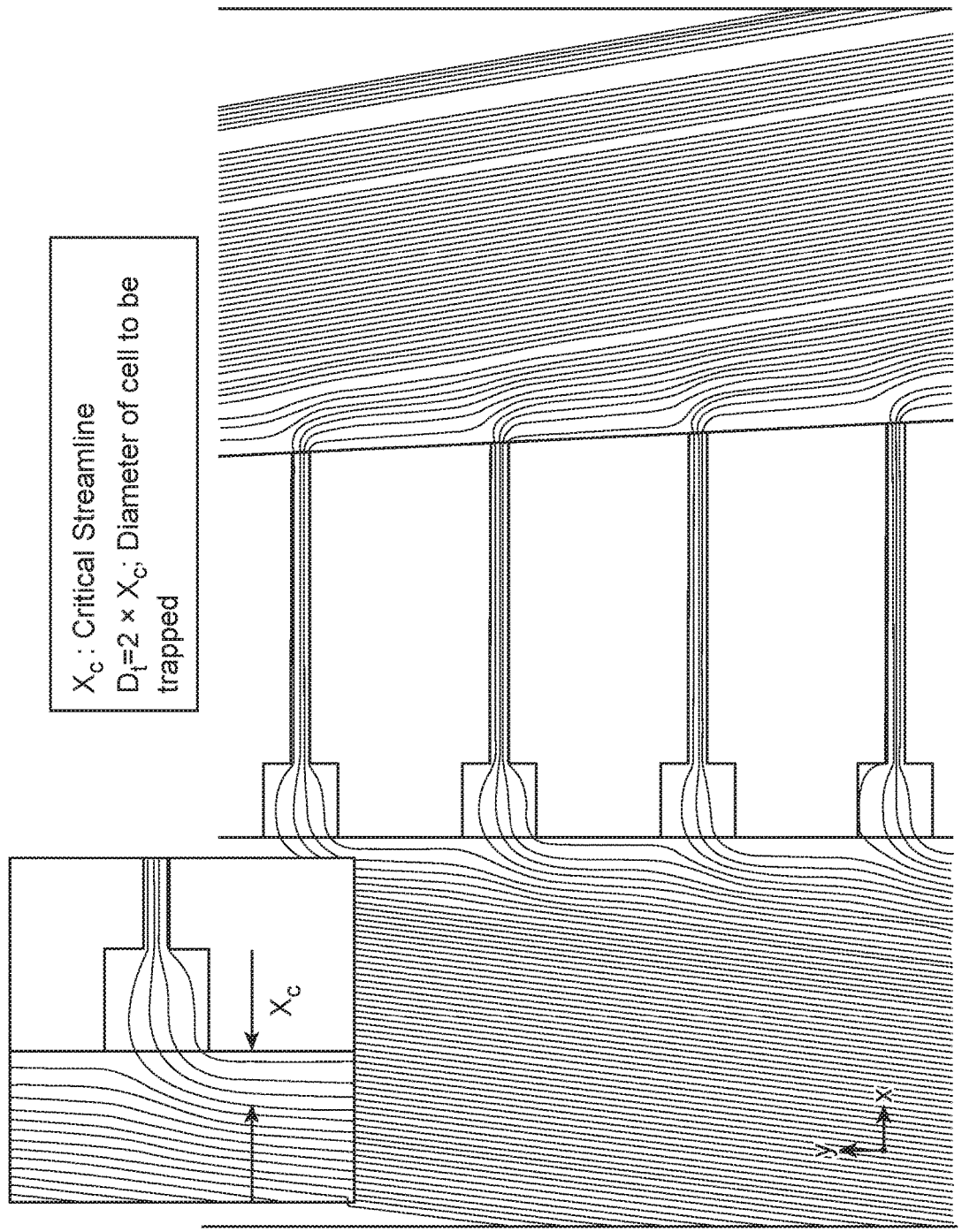
FIG. 3A is a flow diagram through the cell isolation channel and capture channels of the microfluidic device, according to an embodiment of the invention.
Figure 3B:
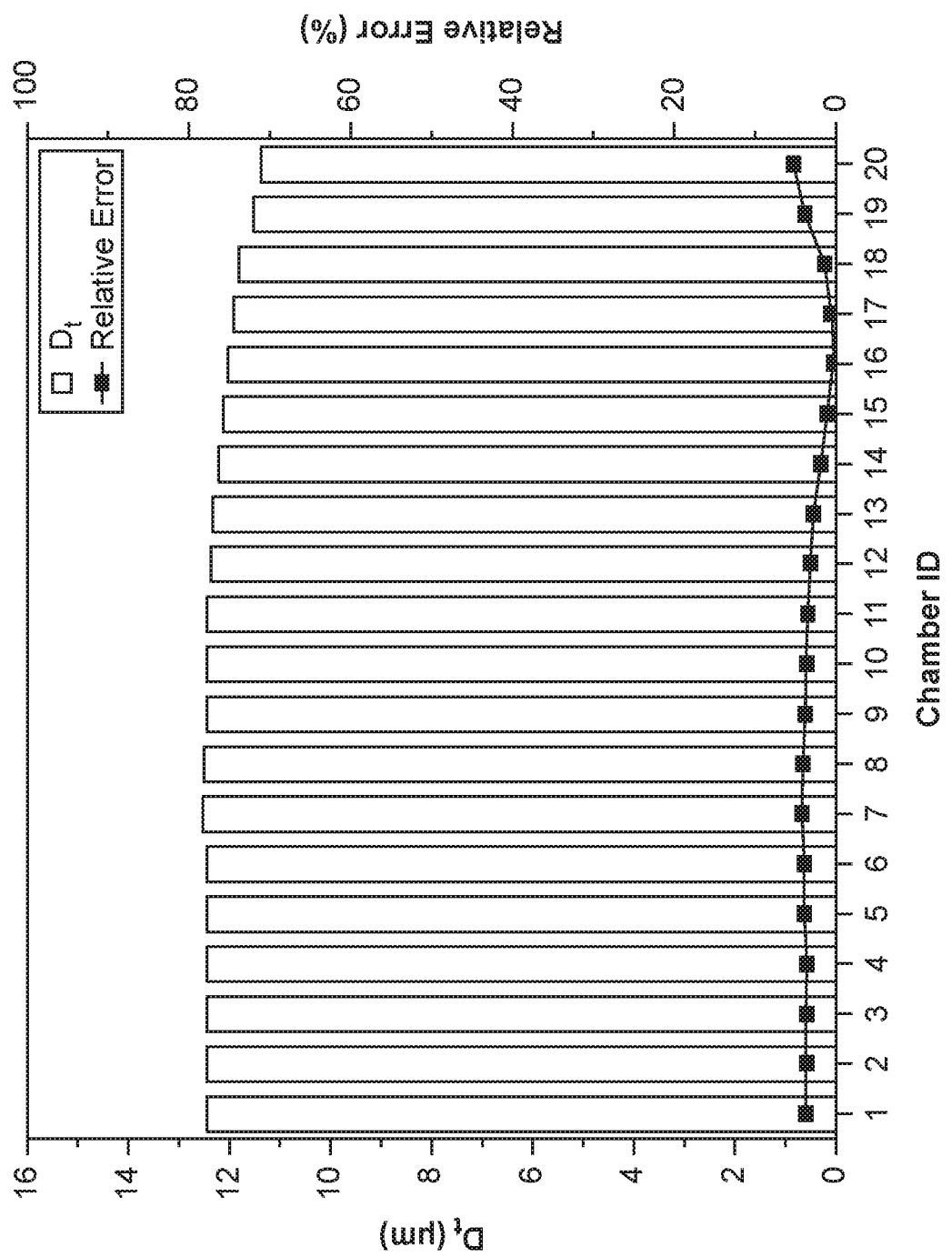
FIG. 3B is a plot showing the dependence of relative error on $D_t$ (μm).
Figure 4:
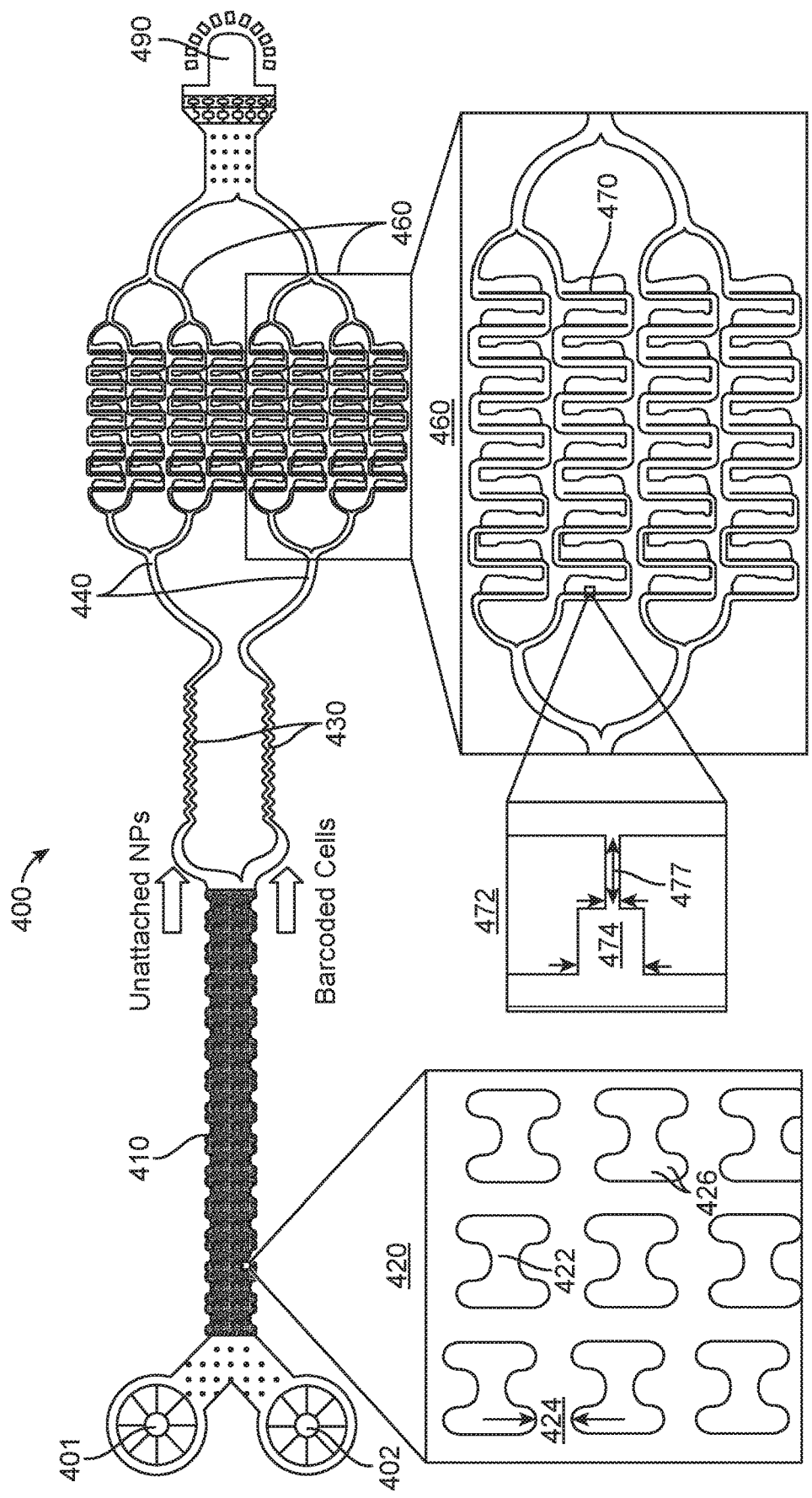
FIG. 4 is a diagram of an embodiment of a DLD separation and T cell trapping microfluidic device, according to another embodiment of the invention.

A numerical simulation has been studied to evaluate the width of the critical streamline ($X_c$) at each trapping room (FIG. 3A). The $D_t$ ($2 \times X_c$) values have been calculated for each room and the corresponding relative errors with a criterion value (12 µm) were determined (FIG. 3B). Thus, in some embodiments, each trap region has been engineered to have around 12 µm of $D_t$ (2×critical streamline).

DLD microfluidic device design is not limited to the one shown in FIG. 2A. For example, another effective device deign is shown in FIG. 4, which (compared to the device in FIG. 2A) has a smaller footprint (1×4 cm vs. 2×6 cm), higher cell trap density (9291 vs. 145 traps/cm$^2$), and is simpler to manufacture (one vs, two layer). This chip (FIG. 4) comprises a sample inlet 401 and a buffer inlet 402, followed by a separation channel 410 comprising a 14 mm-long DLD array 420 for the separation of barcoded T-cells from unattached nanoparticles. After the separation channel, the channel bifurcates into two paths the top is for unattached nanoparticles and the bottom is for barcoded T-cells. The barcoded T-cells are sorted to the bottom, mixed by a mixing channel 430 with a serpentine structure, and distributed via a distribution channel 440 to an array of single-cell traps 460. The unattached nanoparticles are carried across the top path, flowing through features that mirror the bottom path (for balanced flow rate). Finally, the excess buffer solution and unattached nanoparticle are removed at the waste outlet 499. Here, the DLD array 420 uses an "1-shape" pillar design 422 with 12.5 µm gap 424, 45 µm pitch, and 4.5 µm row shift (i.e. $\theta=5.71°$ (426)). To minimize device footprint and increase cell trap density, the pre-focuser and trap design from FIG. 2A is replaced by a modular design, featuring a densely packed 4×10 array of 20 single-cell capture channels 472 (i.e. 800 total trap regions 474). The trap region 474 for the single cell capture is 9 µm in width (W) and the buffer outflow region 477 has a 2. µm width. Guided by numerical simulations, the design of this cell trap array maximizes flow rate into the traps relative to the flow rate through the buffer outflow region 477.

The engineered microfluidic chips described herein enable the barcoded T-cells to be separated, focused, and trapped at the single cell level with high efficiency in a continuous manner. Upwards of eight hundreds of the cells can be captured and a sequent analysis can be carried out on a chip.

Although the microfluidic device has been described with respect to separation of bound and unbound particles for T cell analysis, the device can be used broadly for application to separation of particles in a sample by size and isolating particles for further analysis. Thus, provided herein, according to some embodiments are microfluidic devices designed to separate objects on the basis of physical size and to isolate separated objects for subsequent analysis. The objects can be cells, biomolecules, inorganic beads, or other objects of round or other shape. Typical sizes fractionated can range from 100 nanometers to 50 micrometers; smaller or larger sizes can be fractionated. Use of these arrays can involve continuous flows in one direction, and particles can be separated from the flow direction by an angle which is a monotonic function of their size.

The methods, compositions, devices, and/or systems described herein can be used for high-throughput processing (e.g., chemical and/or enzymatic treatment), purification, isolation, and/or concentration of particles. The methods, compositions, devices, and/or systems described herein can be used to isolate particles with relatively high purity, yield, and/or viability if the particles are living, (e.g., cells or organisms). One or more samples can be applied to one or more inlets on a device. One or more buffers can be applied to one or more inlets on a device. Particles of at least a critical (predetermined) size can be passed through an array of obstacles and be deflected to one outlet, and particles less than the critical size can pass to a region for isolation and subsequent analysis.

In Situ Analysis of Isolated T Cells in the Microfluidic Device

In some embodiments, the device further comprises a sensor to detect a sequence of the barcode to identify the identity of an antigen in an antigen-MHC complex bound to an isolated T cell. In some embodiments, this sensor comprises an optical sensor, such as a camera. In some embodiments, the sensor comprises an electrical signal, such as electrodes. Methods and devices for detection of detectable signals are well known in the art.

To generate detectable signals to discriminate between different barcodes, in some embodiments, probes bound to detectable signals are used. The probes can include a binding region that is specific for a barcode or a section of a barcode. In some embodiments, a series of probes is used to detect a sequence of signals from a barcode that is correlated with the identity of the antigen bound to the isolated T cell.

In some embodiments, the cell is isolated and trapped in the capture channel such that it remains viable. In some embodiments, after analysis of the trapped cell, it can undergo clonal expansion to generate a colony of antigen-specific T cells.

Microfluidic Device Materials and Fabrication

A device can be made from any of the materials from which micro- and nano-scale fluid handling devices are typically fabricated, including silicon, glasses, plastics, and hybrid materials. The flow channel can be constructed using two or more pieces which, when assembled, form a closed cavity (preferably one having orifices for adding or withdrawing fluids) having the obstacles disposed within it. The obstacles can be fabricated on one or more pieces that are assembled to form the flow channel, or they can be fabricated in the form of an insert that is sandwiched between two or more pieces that define the boundaries of the flow channel. Materials and methods for fabricating such devices are known in the art.

In some cases, the flow channel can be preferably formed between two parallel, substantially planar surfaces, with the obstacles formed in one of the two surfaces (e.g., by etching the surface to remove material that originally surrounded the non-etched portions that remain as obstacles). The obstacles can have a substantially constant cross-section along their length, it being recognized that techniques used to fabricate the obstacles can limit the uniformity of the cross section.

In some embodiments, a device is made by hot embossing PMMA and polycarbonate. Due to their low cost and compatibility with replication-based fabrication methods, thermoplastics can represent an attractive family of materials for the fabrication of lab-on-a-chip platforms. A diverse range of thermoplastic materials suitable for microfluidic fabrication is available, offering a wide selection of mechanical and chemical properties that can be leveraged and further tailored for specific applications. High-throughput embossing methods such as reel-to-reel processing of thermoplastics is an attractive method for industrial microfluidic chip production. The use of single chip hot embossing can be a cost-effective technique for realizing high-quality microfluidic devices during the prototyping stage. Methods for the replication of microscale features in two thermoplastics, polymethylmethacrylate (PMMA) and/or polycarbonate (PC) are described herein using hot embossing from a silicon template fabricated by deep reactive-ion etching. Further details can be found in "Microfluidic device fabrication by thermoplastic hot-embossing" by Yang and Devoe, Methods Mol. Biol. 2013; 949: 115-23, which is hereby incorporated by reference herein in its entirety. In some cases, a device is made of polypropylene.

In some cases, a device comprises a polymer. In some cases, a device is made by injection molding. In some cases, a device is manufactured by a photolithographic technique. In some cases, a device is manufactured by soft embossing. In some cases, the embossing occurs on a polymer chip. In some cases, a device comprises plastic.

A device can be sealed and bonded in any suitable manner. The main challenge can be bonding planar microfluidic parts together hermetically without affecting the shape and size of micro-sized channels. A number of bonding techniques such as induction heating are suitable. The channels can be fabricated by using Excimer laser equipment. Further details can be found in "Sealing and bonding techniques for polymer-based microfluidic devices" by Abdirahman Yussuf, Igor Sbarski, Jason Hayes and Matthew Solomon, which is hereby incorporated by reference herein in its entirety.

Further bonding techniques include Adhesive Bonding, Pressure sensitive tape/Lamination, Thermal Fusion Bonding, Solvent Bonding, Localized welding, Surface treatment and combinations thereof. Further details can be found in "Bonding of thermoplastic polymer microfluidics" by Chia-Wen Tsao and Don L. DeVoe, Microfluid Nanofluid (2009) 6:1-16, which is hereby incorporated by reference herein in its entirety.

A device can be fabricated in any suitable manner. Some techniques include Replica molding, Softlithography with PDMS, Thermoset polyester, Embossing, Injection Molding, Laser Ablation and combinations thereof. Further details can be found in "Disposable microfluidic devices: fabrication, function and application" by Gina S. Fiorini and Daniel T. Chiu, BioTechniques 38:429-446 (March 2005), which is hereby incorporated by reference herein in its entirety. The book "Lab on a Chip Technology" edited by Keith E. Herold and Avraham Rasooly, Caister Academic Press Norfolk UK (2009) is a resource for methods of fabrication, which is hereby incorporated by reference herein in its entirety. A device can be manufactured by cast molding or reactive injection molding.

Exemplary materials for fabricating the devices of the invention include glass, silicon, steel, nickel, polymers, e.g., poly(methylmethacrylate) (PMMA), polycarbonate, polystyrene, polyethylene, polyolefins, silicones (e.g., poly(dimethylsiloxane)), polypropylene, cis-polyisoprene (rubber), poly(vinyl chloride) (PVC), poly(vinyl acetate) (PVAc), polychloroprene (neoprene), polytetrafluoroethylene (Teflon), poly(vinylidene chloride) (SaranA), and cyclic olefin polymer (COP) and cyclic olefin copolymer (COC), and combinations thereof. Other materials are known in the art. For example, deep Reactive Ion Etch (DRIE) can be used to fabricate silicon-based devices with small gaps, small obstacles and large aspect ratios (ratio of obstacle height to lateral dimension). Thermoforming (embossing, injection molding) of plastic devices may also be used. Additional methods include photolithography (e.g., stereolithography or x-ray photolithography), molding, embossing, silicon micromachining, wet or dry chemical etching, milling, diamond cutting, Lithographic Galvanoformung and Abformung (LICA), and electroplating. For example, for glass, traditional silicon fabrication techniques of photolithography followed by wet (KOH) or dry etching (reactive ion etching with fluorine or other reactive gas) may be employed. Techniques such as laser micromachining can be adopted for plastic materials with high photon absorption efficiency. This technique is suitable for lower throughput fabrication because of the serial nature of the process. For mass-produced plastic devices, thermoplastic injection molding, and compression molding can be suitable. Conventional thermoplastic injection molding used for mass-fabrication of compact discs (which preserves fidelity of features in sub-microns) may also be employed to fabricate the devices. For example, the device features are replicated on a glass master by conventional photolithography. The glass master is electroformed to yield a tough, thermal shock resistant, thermally conductive, hard mold. This mold serves as the master template for injection molding or compression molding the features into a plastic device. Depending on the plastic material used to fabricate the devices and the requirements on optical quality and throughput of the finished product, compression molding or injection molding may be chosen as the method of manufacture. Compression molding (also called hot embossing or relief imprinting) can have the advantage of being compatible with high molecular weight polymers, which can be excellent for small structures and may replicate high aspect ratio structures but has longer cycle times. Injection molding can work well for low aspect ratio structures and can be suitable for low molecular weight polymers. A device can be made using any of the materials described herein. In some cases, the surface of the (plastic) device is treated to make it hydrophilic and/or wettable. Surfaces in devices, e.g., microfluidic devices, can play a critical role because they can define properties such as wetting, adsorption and repellency of biomolecules, biomolecular recognition using surface-immobilized receptors, sealing and bonding of different materials. In some cases, two types of treatments can be used to modify the surface properties of a device, e.g., a microfluidics device: wet chemical treatments and gas phase treatments. Wet treatments can be simple in terms of infrastructure requirements; they can be flexible and fast to develop from a research standpoint. Surface treatment of a device, e.g., a microfluidic device, for production can be achieved using dry processes based on plasma and chemical vapor deposition. These treatments can eliminate the need for rinsing and drying steps, have high throughput capability and are highly reproducible.

Serial Analysis of Antigen-Specific T Cells

In some embodiments, instead of using a DLD device, the identity of antigen-specific cells can be determined by identifying antigen-specific T cells using a NP-antigen-MHC complexes serially by antigen type. Thus, rather than exposing a T cell population to a library of barcoded NP-antigen-MHC complexes simultaneously, a subset of NP-antigen-MHC complexes containing the same antigen are exposed to a T cell population and T cells bound to nanoparticles (e.g., magnetic beads) are separated. The remaining T cells are exposed to the next subset of NP-antigen-MHC complexes that each contain an identical antigen that is different from the earlier subset. This process can be repeated serially to separate and analyze many populations of antigen-specific T cells. The basic method for magnetic separation as described herein can be used.

After performing this serial method for searching through a heterogeneous mixture of lymphocytes for antigen-specific T cell populations and separating them from the mixture, the cells can then be stained using a live/dead cell staining reagents so that the live cells become fluorescent. The separated cells are then introduced into a standard hemocytomer chip for counting (ATCH), or they are further analyzed.

According to some embodiments, of the invention, provided herein is a method for isolating antigen-specific T cells, comprising: preparing one or more sets of NP-antigen-MHC complexes comprising an identical antigen, wherein said antigen differs between each set, inclubating one of said one or more sets of NP-antigen MHC complexes with a sample comprising T cells; separating T cells that bind to said NP-antigen-MHC complexes from unbound T cells; and analyzing said set of T cells bound to said NP-antigen-MHC complexes. In some embodiments, the method further comprises staining said T cells bound to said NT-antigen-MHC complexes. In some embodiments, the stain is a live/dead cell stain. In some embodiments, said step of analyzing comprises counting said cells. In some embodiments, counting said cells is performed using a hemocytometer. In some embodiments, the method is repeated using a different set of NP-antigen-MHC complexes on T cells that did not bind to NP-antigen-MHC complexes from a previous set.

Figure 5:
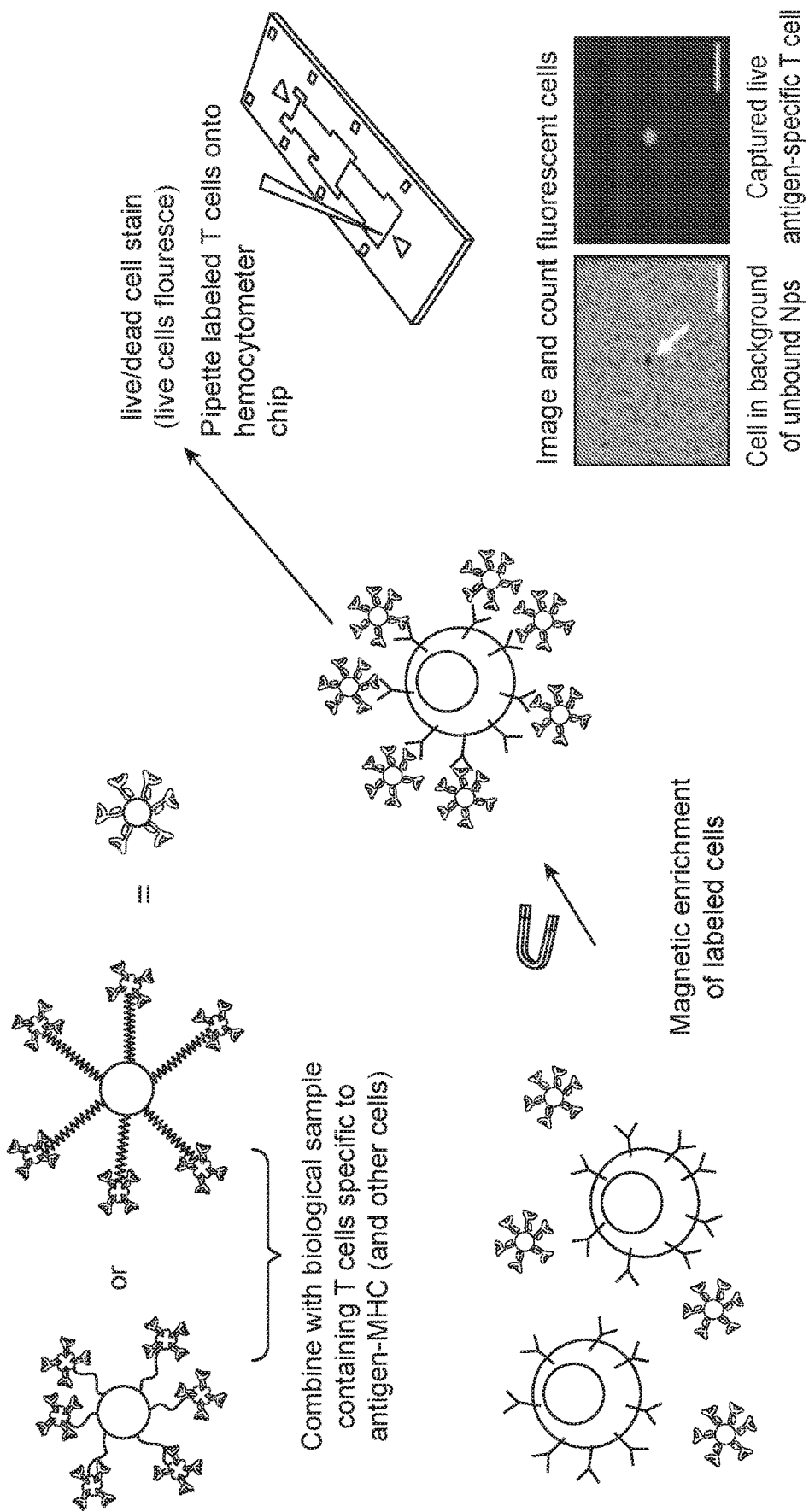
FIG. 5 is an illustration of reagents used and steps for a serial method of identification of T cell antigen specificity, according to an embodiment of the invention.

An embodiment of the method is illustrated in FIG. 5. Antigen-major histocompatibility (MHC) tetramer complexes are appended to magnetic nanoparticles via either standard linker molecules or ssDNA oligomers comprise the primary reagents for capturing antigen-specific T cells. These reagents are combined with a heterogeneous T cell mixture. The MHC tetramer reagents bind to those T cells that have a T cell receptor (TCR) specific to the peptide antigen presented by the MHC. Labeled cells and unbound nanoparticles are separated from unlabeled cells using a magnet. The captured cells and nanoparticles are re-suspended in solution, and pipetted onto a cytometry chip. Bright field imaging shows a dark spot on a background of unbound nanoparticles. Fluorescence imaging reveals that the dark spot is a live, antigen-specific T cell. The T cells can be enriched by this serial method with close to 100% efficiency, while with low background noise.

The basic capture agents are as described herein. In some embodiments, the linker between the MHC tetramer and the nanoparticle is DNA, and information can be encoded into the DNA for subsequent analysis of the captured antigen-specific T cells. However, for very challenging biospecimens, it may be necessary to minimize any non-selective binding of the capture agents with background cells. This becomes increasingly important as the quality of the biospecimens degrades, many of the cells, while alive, are barely viable. Thus, in some embodiments, non-fouling polymers such as PEG, can be used to replace DNA as a linker to minimize background noise. In addition, in some embodiments, a biotinylated MHC is directly bound to the nanoparticle. This can help to reduce background noise, without compromising T cell detection sensitivity.

A comparison between this embodiment of antigen-specific T cell identification using serial addition of individual antigens subsets from a library of antigen/MHC tetramer/nanoparticle constructs (Antigen-specific T cell Hemocytometry (ATCH)) and the NP-barcoded NACS method are provided in Table 1 below.

TABLE 1

Comparison of NP-barcoded NACS with ATCH

| | Live cell confirmation | Confirmation of Antigen Specificity | Parallel Analysis | Serial Analysis | Challenging Biospecimens | Quantitative | Time to analyze for 40 antigen-specific populations | Requires custom microfluidic device | Cells available for additional analysis | Noise (detection threshold of a cell population from $10^4$ cells) |
|---|---|---|---|---|---|---|---|---|---|---|
| ATCH | y | | | y | better | y | 1-2 days | No | y | 5 parts in $10^4$ |
| NP-barcoded NACS | | y | y | | | y | 1 day | y | y | 3 parts in $10^4$ |

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W. H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B(1992).

Example 1

NP-Neoantigen-MHC Complex Library Formation (NP-NACS)

For each barcoded nanoparticle, required amounts of each reagent are as follows:
1 µl peptide (4 mM)
4 µl MHC (10 µM)
1 µl SAC-modified DNA (10 µM)
5 µl MyOne Nanoparticles (1 µM stock conc.)
1 µl DNA (100 µM stock conc.)
Binding and washing (B&W) buffer (1×): 5 mM Tris-HCl (pH 7.5), 0.5 mM EDTA, 1 M NaCl
Dynabeads™ MyOne™ Streptavidin T1 (catalog #: 65601)
Costar Transwell Permeable Supports (3.0 µm polyester membrane), Polystyrene Plates
CellTracker™ Orange CMRA Dye (C34551)—a live-cell dye that does not overlap with fluorophores used for barcoding (Alexa Fluor 488, Alexa Fluor 750, and Cy5 dyes)

Per peptide equivalent, aliquot 5 µl of MyOne Nanoparticles (1 µM stock conc.) solution. Wash particles with 2×volume of 1×B&W buffer three times. Resuspend particles back to 4×volume in B&W buffer. Per peptide equivalent, aliquot 20 µl of the solution into one tube. Add 1 µl of the respective biotin-DNA barcode to each equivalent. Mix and rotate tubes at room temperature for 30 minutes. Wash with 2×volume B&W buffer two times. Wash with 2×volume PBS once. Resuspend each equivalent in 20 µl PBS containing 2 mM $MgCl_2$.

In a 96 well-plate, add 1 µl of peptide (4 mM) into a well. Mix 4 µl MHC (10 µM) with 75 µl PBS (0.05% F68, pH=7.56) and add this mixture into the well. Expose sample to UV light at 4-8 mW/$cm^2$ for 1 hour.

Once UV exchange is complete, spin down sample (~14,000 g, 5 minutes). Extract supernatant into a new tube. Add 1 µl streptavidin with DNA modification (10 µM) to each tube and rotate tube at room temperature for 30 minutes.

Streptavidin magnetic nanoparticle (1 µm, ThermoFisher scientific) was mixed with biotin-DNA at 1:20 ratio to obtain nanoparticle-DNA. Excess DNA was removed by washing the magnetic nanoparticle for 3 times. In parallel, MHC neo-antigen library was added to ssDNA-SAC at 4:1 ratio to form the DNA-MHC tetramer. Equal amount (in terms of DNA ratio) of nanoparticle-DNA and DNA-MHC tetramer were hybridized at 37° C. for 30 min to generate a barcoded nanoparticle MHC neo-antigen library.

For each peptide equivalent, mix 10 µl of the respective nanoparticle solution (from the 20 µl prepared in step 3) with 10 µl PBS containing 20 mM $MgCl_2$. Then add the MHC-tetramer solution from step 4 (~80 µl) for a total volume of approximately 100 µl. Mix contents thoroughly, and rotate at 37° C. for 30 minutes. Then wash tubes with 100 µl PBS (containing 0.1% bovine serum albumin (BSA) and 2 mM $MgCl_2$). Resuspend in 20 µl of the same wash buffer. A small aliquot of the particles (~2 µl) may be diluted with the wash buffer to a final volume of 10 µl, and then inserted into cytometer chip to inspect for aggregation. During preparation of the nanoparticle-barcoded library, one may observe large aggregates, approximately similar in size to a cell. These complexes can provide false positive reads during application of the microfluidics chip. Therefore, these aggregates must be filtered out prior to mixing of the nanoparticle-barcoded library with T cells.

Alternatively, streptavidin magnetic nanoparticle (1 μm, ThermoFisher scientific) was mixed with biotinylated MHC neo-antigen at a ratio of 1:4 to 1:8 at room temperature for 30 min. The labeled nanoparticle was washed with PBS for 1-2 times to remove any free biotinylated MHC. This forms NP-antigen-MHC complexes without a barcode.

Figure 6:
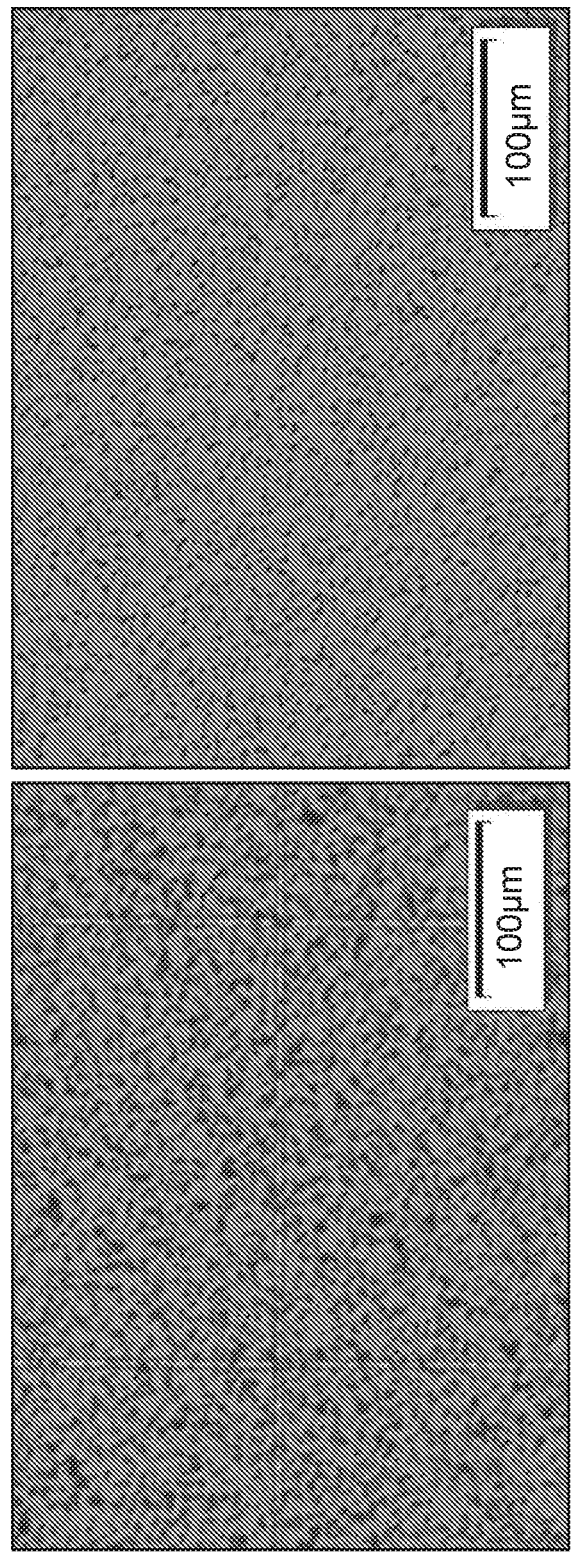
FIG. 6 is an image of a nanoparticle-barcoded library. Left: nanoparticle-barcoded library mixed together, prior to filtration, highlighting presence of cell-sized aggregates. Right: nanoparticle-barcoded library mixed together with 3 μm filtration, highlighting effectiveness filtration.

In order to remove aggregates from the nanoparticle-barcoded library, the particle suspension was transferred onto a 3.0 μm polyester membrane (taken from Costar polystyrene plates). The particles were spun down and the filtrate collected in a 1.7 ml Eppendorf tube. PBS was added (containing 0.1% BSA and 2 mM $MgCl_2$) on the membrane and spin down again. This step was repeated twice, each time rotating the filter 180 degrees. The filtrate was collected and the total volume was decreased to 20 μl. FIG. 6 shows cytometer chip images of nanoparticle-barcoded library. Left: nanoparticle-barcoded library mixed together, prior to filtration, highlighting presence of cell-sized aggregates. Right: nanoparticle-barcoded library mixed together with 3 μm filtration, highlighting effectiveness filtration. As illustrated in FIG. 6, filtering is an effective method of removing cell-sized nanoparticle aggregates.

Example 2

Library Mix with Non-Reactive Human PBMCs (Negative Control)

A nanoparticle-barcoded library was mixed with non-reactive human PBMCs to screen for false positive binding. A nanoparticle-barcoded library for 27 peptides was mixed with human PBMCs which have no reported reactivity to any of the included peptides. Specifically, 100 μl of cells were extracted from non-reactive human PBMC cell solution, and mixed with 20 μl of filtered nanoparticles. This solution was rotated at room temperature for 15 minutes to mix. The solution was then washed with 2×volume PBS (containing 5% BSA with 2 mM $MgCl_2$), and resuspended in the same buffer to 50 μl. Cells are stained with calcein green dye. Particles were mixed with Cy5 dye for all three barcode positions prior to mixing with cells.

Figure 7:
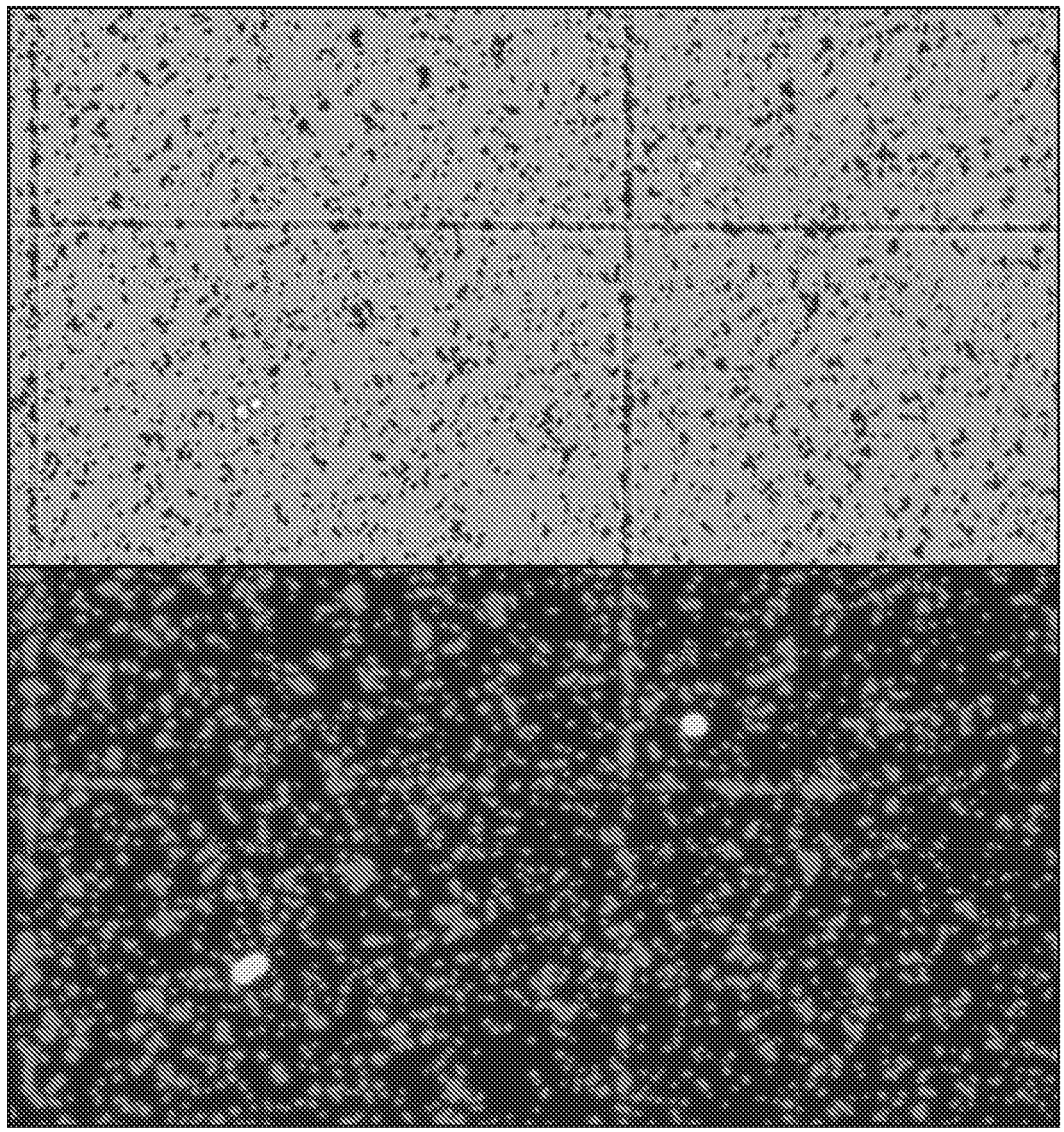
FIG. 7 is an image of a nanoparticle-barcoded library mixed with non-reactive human PBMCs.

FIG. 7 shows a brightfield image (top) and a fluorescence image (bottom) of the resulting mixed solution. Neoantigen-specific T cells will appear dark in color when barcoded, since the nanoparticles themselves are black. In contrast, consistent with FIG. 7, cells with no reactivity to the nanoparticle-barcoded library does not associate with any nanoparticles.

Example 3

Capture Efficiency of Antigen-Specific T Cells

The barcoded NP-antigen-MHC complex library was validated by employing selective capture of Mart-1 antigen specific T cells from a mixture of cells. FIG. 8, panel A shows a schematic illustration of NP-Mart-1 tetramer for capture of Jurkat cells transduced with a Mart-1 specific T-cell receptor. FIG. 8, panel B shows mixed Jurkat (stained green) and CiBM U87 cells (stained blue). The NP-Marti tetramer is incubated with the mixed cell population and magnetically enriched with cells from the supernatant shown in FIG. 8, panel C, and from the magnetic pulldown shown in FIG. 8, panel D.

Example 4

Sensitivity Comparison of NP-NACS and FACS Methods

Figure 9:
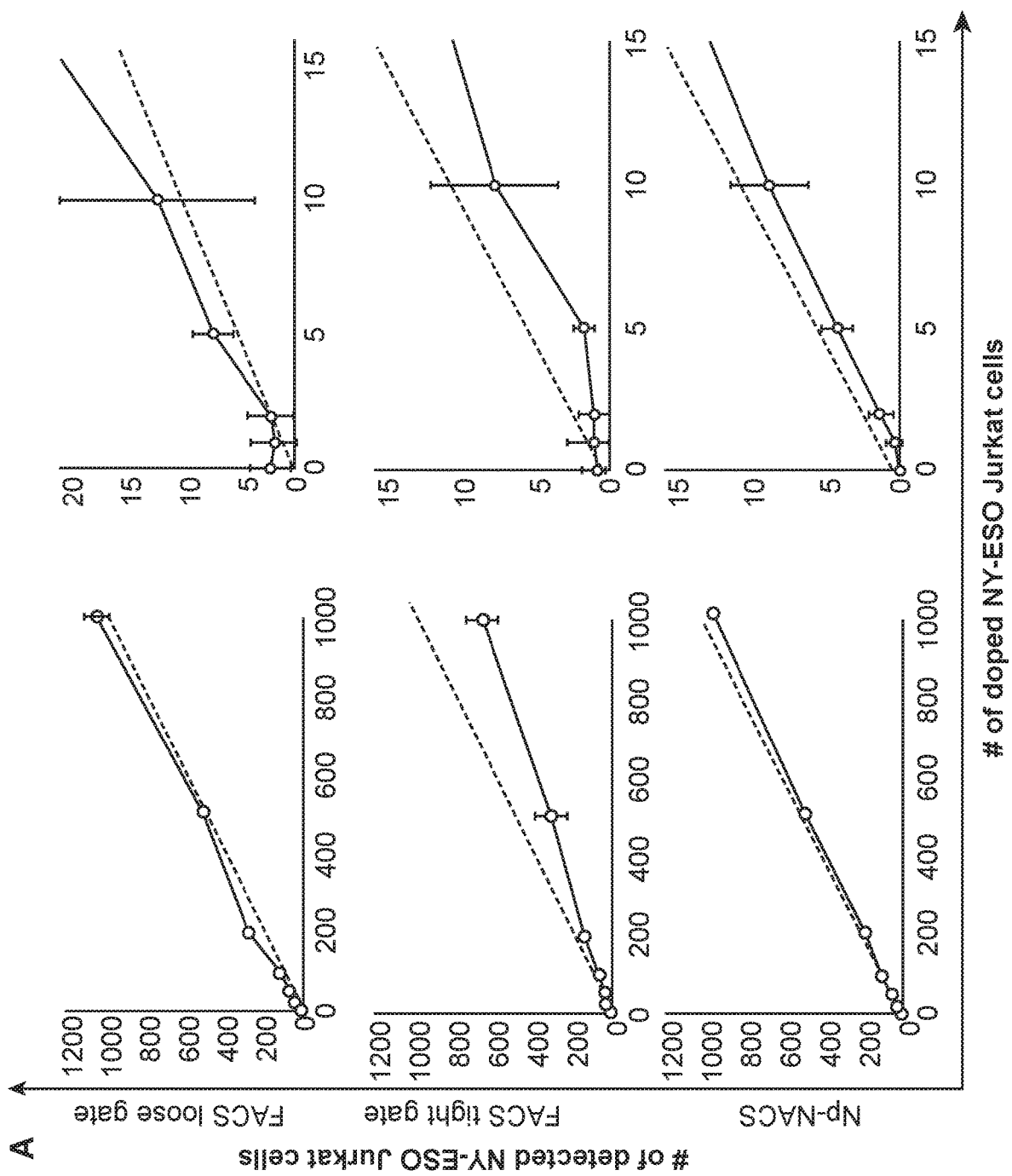
FIG. 9 shows data from a sensitivity comparison of NP-MACS and FACS methods. A. Plot of number of NY-ESO Jurkat T cells detected by FACS and NP-MACS methods. Right column is the zoomed in images of left column in the lower cell number. Data are demonstrated as mean±standard deviation. Gray dash line indicates the theoretical cell number to be detected by the two methods. B. Typical FACS plots. The loose gate is determined by visual separation of double-fluorescent positive Jurkat T cells from double-fluorescent negative Jurkat T cells (upper left). The loose gate results APC fluorescent leaks to the single PE-NY-ESO controls (upper right). The tight gate is set to eliminate any possible leak of double-fluorescent positive signals from non-stained Jurkat T cells, as well as PE-NY-ESO or APC-NY-ESO single stain controls (lower left). However, the tight gate results the decrease of double-fluorescent positive cells (lower right). C. Typical image of NP-NACS method. The pulldown cell is covered by magnetic nanoparticles (left) and stained by green fluorescence (right). Scale bar is 50 μm.
Figure 9:
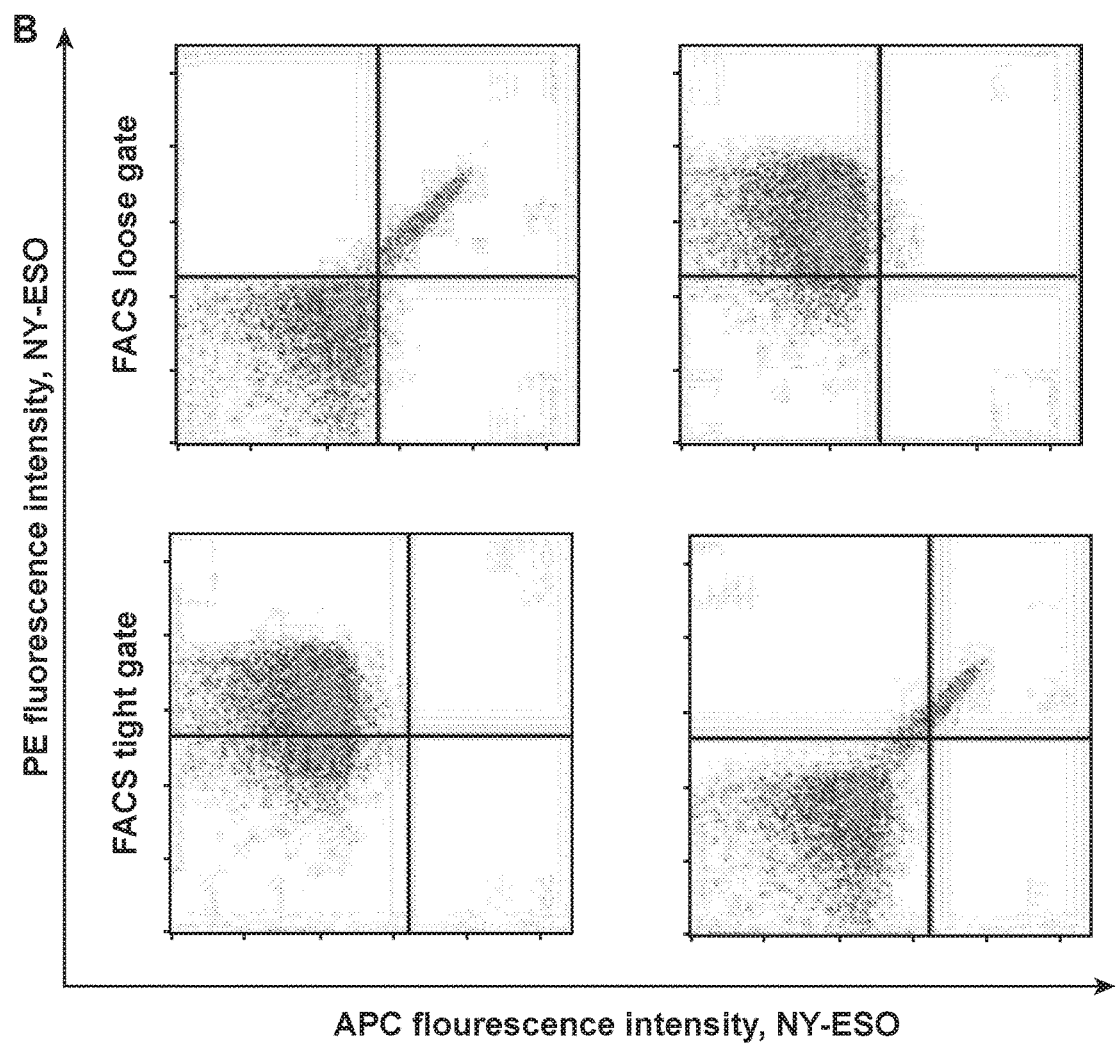
Figure 9:
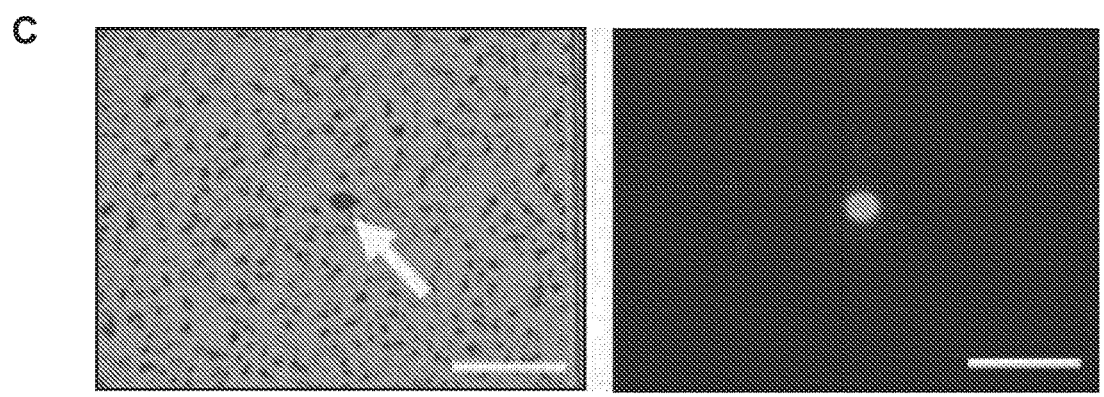

The sensitivity of NP-NACS and FACS methods were compared. FIG. 9, panel A shows the number of NY-ESO Jurkat T cells detected by FACS and NP-NAGS methods. Right column is the zoomed in images of left column in the lower cell number. Data are demonstrated as mean±standard deviation. Gray dash line indicates the theoretical cell number to be detected by the two methods. FIG. 9, panel B, shows representative FACS plots. The loose gate is determined by visual separation of double-fluorescent positive Jurkat T cells from double-fluorescent negative Jurkat T cells (upper left). The loose gate results APC fluorescent leaks to the single PE-NY-ESO controls (upper right). The tight gate is set to eliminate any possible leak of double-fluorescent positive signals from non-stained Jurkat T cells, as well as PE-NY-ESO or APC-NY-ESO single stain controls (lower left). However, the tight gate results the decrease of double-fluorescent positive cells (lower right). FIG. 9, panel C. Typical image of NP-NACS method. The pulldown cell is covered by magnetic nanoparticles (left) and stained by green fluorescence (right). Scale bar is 50 μm.

Example 5

CD8+ T Cell Pulldown and Analysis Via Hemocytometer

Cells from PBMCs or TILs were flow cytometry-sorted, purifying for viable (live/non-apoptotic), CD8+, and CD3+. After removing sheath fluid and replacing with media, sorted cells are treated with DNAse (20 μg/mL, 20 min at 37° C. in media containing 2 mM $MgCl_2$), washed once in serum-free media, stained using CellTracker dye (10 μM, 15 min at 37° C. in serum-free media), and washed again in serum free-media. Cells are resuspended in PBS (containing 5% BSA with 2 mM $MgCl_2$) at 1 million cells/ml prior to mixing with nanoparticle-barcoded library.

Isolated cells are incubated with each individual NP-NACS library at room temperature for 15-30 min, Neo-antigen specific cells were enriched by magnet pulldown. The non-captured T cells in the supernatant was collected for further incubation with other NP-NACS library element. The enriched T cells were washed by PBS once to remove any non-specific cell pulldown. Cells were then loaded into a cell hemocytometer. The whole area in the hemocytometer chip was imaged to obtain the total pulldown cell number. Healthy donor PBMC and/or PBMC from an unrelated male melanoma patient were used as control to obtain the background.

Example 6

CD8+ T-Cell Capture from a Healthy Donor

Figure 10:
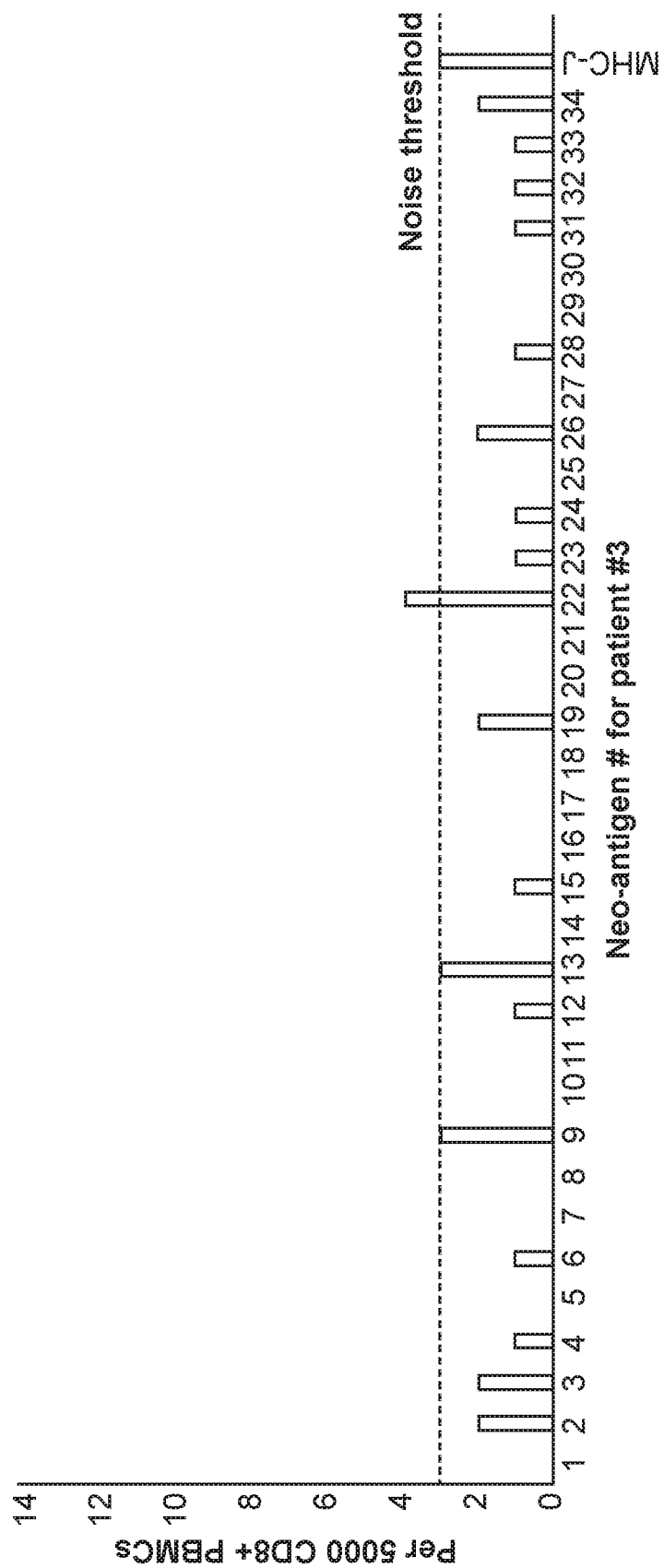
FIG. 10 shows the results of control experiments in which the nanoparticle-barcoded NACS library designed for patient #3 was utilized to capture CD8+ PBMCs from a healthy donor.

FIG. 10 shows the results of control experiments in which the nanoparticle-barcoded NACS library designed for patient #3 was utilized to capture CD8+ PBMCs from a healthy donor. Average pulled-down T cells from healthy donor PBMC was 0.9±1.1 (mean±standard deviation). The noise threshold was set at average plus two standard deviations.

Example 7

TIL and PBMC Analysis During Treatment Using NP-NACS

A TIL and PBMC analysis of Patient #3 over the course of response to anti-PD-1 therapy, using the NP-barcoded NACS library to enumerate neoantigen-specific CD8+ T cell populations.

Figure 11:
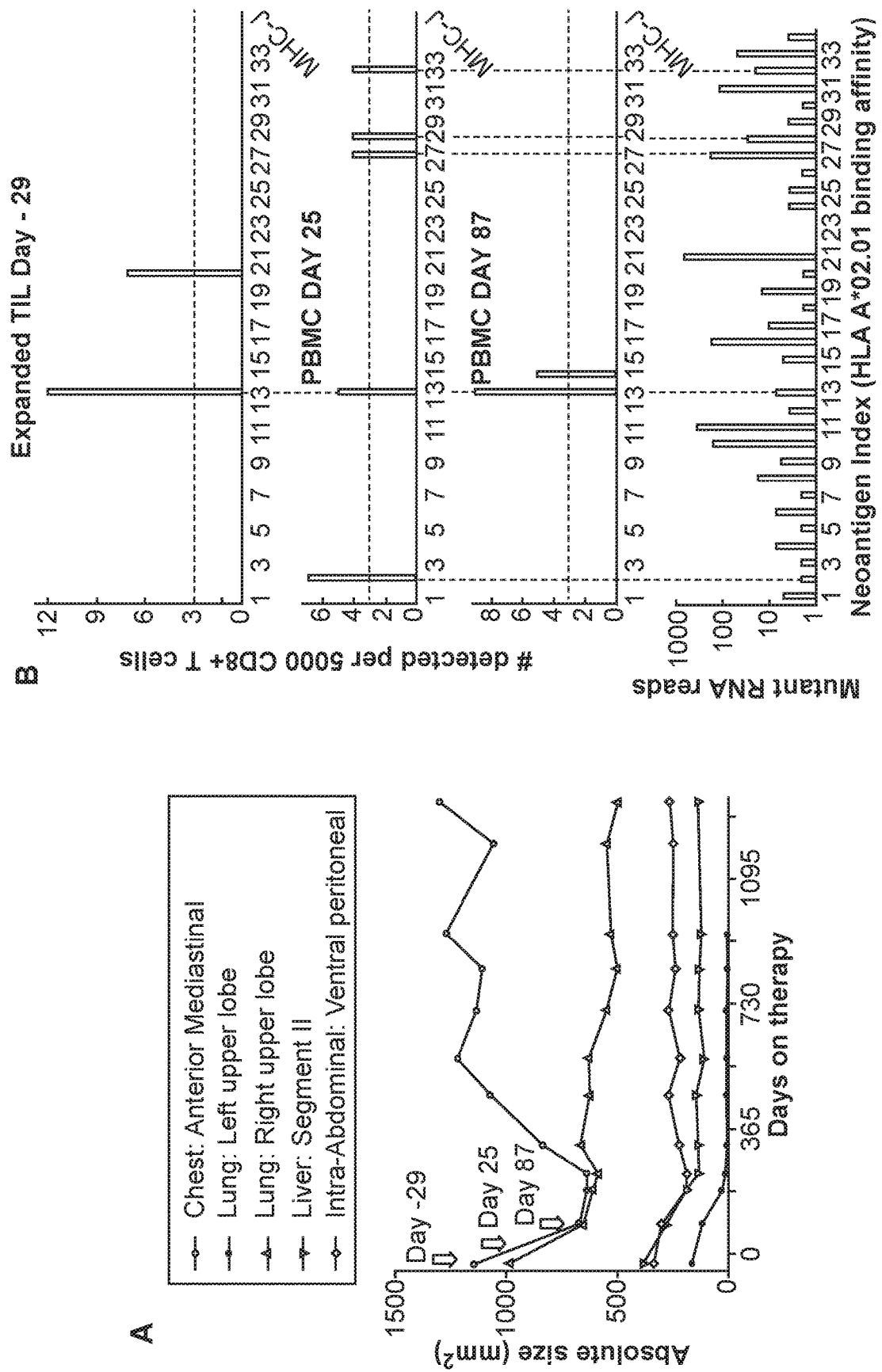
FIG. 11 shows the results of TIL and PBMC analysis of Patient #3 over the course of response to anti-PD-1 therapy, using the NP-barcoded NACS library to enumerate neoantigen-specific CD8+ T cell populations.

FIG. 11, panel A shows timeline of the lesion size of chest, lung, liver and intra-abdominal in Patient #3. Day 0 corresponds to the start of anti-PD-1 therapy. A baseline tumor biopsy (indicated by the purple arrow) was collected for genomic and transcriptomic analysis at day −29. Black dots represent CT-scan measurement dates, while the arrows correspond to the time points of analysis, and are color coded for the bar graphs in FIG. 11, panel B. FIG. 11, panel B shows the neoantigen-specific T cell populations detected from expanded TILs collected from baseline (top graph) and PBMCs over the course of the therapy (middle two graphs), along with mutation-containing mRNA read counts for the mutant proteins (bottom graph) from the baseline RNA-seq. The horizontal dashed lines in the TIL and PBMC analysis graphs represent the signal threshold above which the identification of a T cell population is statistically significant, which is determined in Example 6 (see FIG. 10). The vertical gray dashed lines indicate T cell populations detected across the different time points and patient materials, and their correlation with RNA transcripts reads. Conditional antigen (MHC-J) was used as an internal control.

Example 8

Detailed Operation Protocols of Microfluidic Device

To remove air and any blocking particles from the ULD device, four reagents (800 µl each) were sequentially injected into the DLI) device through the output, at a rate of 3 ml/hr: ethanol (to remove bubbles), PBS (containing 3% F68, to block channel), PBS (neat, to wash away F68), and PBS (containing 5% BSA, 20 mM $MgCl_2$). During this step, the device was examined under the microscope for bubbles. As reagents filled the device, ethanol, 3% F68 PBS, and neat PBS were removed at the sample and buffer reservoir, while PBS (containing 5% BSA, 20 mM $MgCl_2$) is left inside the device and reservoir.

For the duration of the analysis, the device was operated by pulling at rate of 0.05-0.1 ml/hour at the device outlet. Throughout the analysis, the buffer reservoir is kept higher or equal to the height of the sample reservoir—this ensures that free particles will not leak into the trap region. The mixture of barcoded T-cells and unattached nanoparticles were introduced into the device by adding the mixture to the sample inlet. Unattached nanoparticles would be separated and removed from the barcoded T-cells, while barcoded cells would be trapped in the cell traps.

Figure 12:
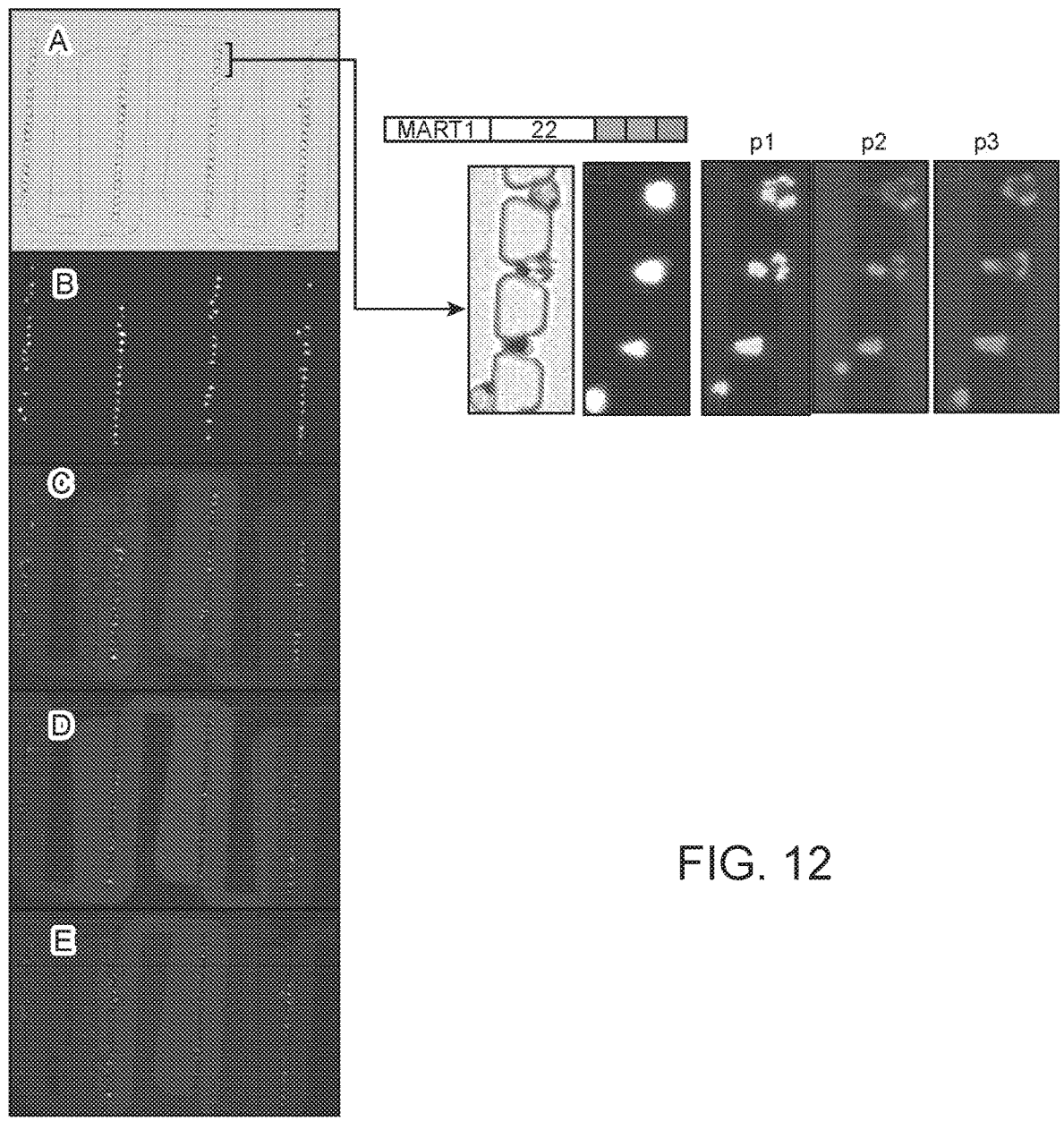
FIG. 12 shows the results of the successful isolation and decoding of a Mart-1-specific Jurkat cells.

After cell loading and trapping sufficient cells, first round DNA barcoding dye was introduced to the buffer channel. The device was then incubated at 37° C. for 15 min, followed by washing with PBS (containing 5% BSA, 20 mM $MgCl_2$) at RT for 1 min through the buffer inlet. The cell traps were then imaged under microscope to obtain the first round barcode. Second round DNA barcode (containing first round displacement DNA and second round DNA barcoding dye) was introduced through the buffer inlet, using the same 37° C. incubation, RT washing and imaging procedures described in the first step. Similarly, third or even more rounds of DNA barcoding can be performed. An example of such analysis is illustrated in FIG. 12, which uses the devices described in FIG. 4. Here, Mart-1-specific Jurkat cells were exposed to a 27-element nanoparticle library and the on-chip barcode analysis successfully decoded the Mart-1 barcode (green-purple-red) in 90% of cells.

After cell barcoding, the syringe pump was stopped, and the device was disposed in the biohazard waste.

Example 9

Application of Microfluidics Chip for Capture of MART1 Jurkat Cells

A nanoparticle-barcoded library for 27 peptides was prepared (barcode #22 associated with the MART1 peptide). This library was mixed with MART1 Jurkat cells, and then flowed through the microfluidics chip. FIG. 12, panel A shows a brightfield image of cells trapped within device. CellTracker™ orange dye fluorescence, was added to the cells to shows the presence of live cells within traps (FIG. 12, panel B). In FIG. 12, panels C-E images of combined FITC, Cy5, and Cy7 fluorescence channels for respective barcode positions 1, 2, and 3 are shown. The inset contains magnified views of sections A-E in their respective order.

Example 10

DLD & Neoantigen Identification

Figure 13:
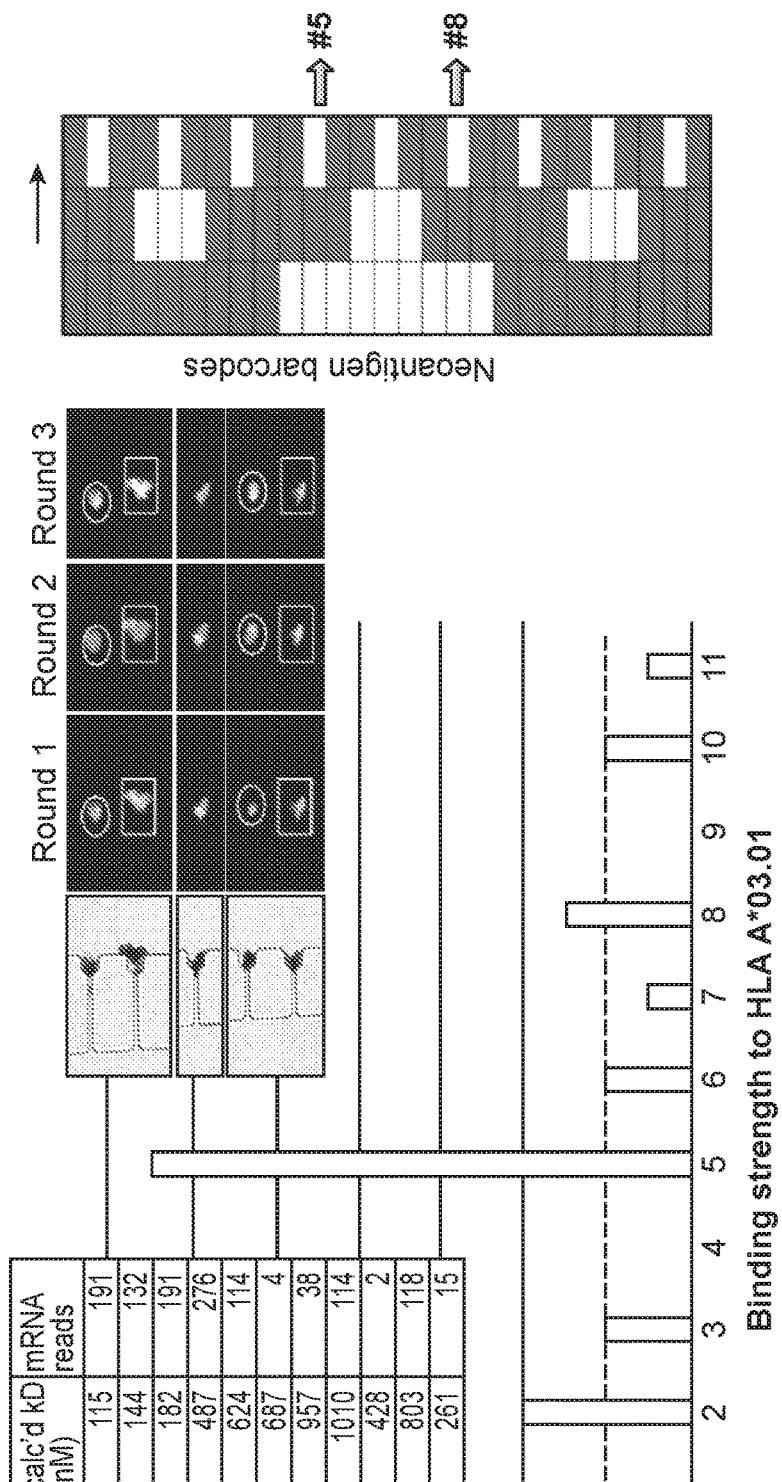
FIG. 13 shows results from the application of the microfluidic chip described herein for the separation, isolation, and analysis of neoantigen-specific CD8+ T cells, collected from the brain tumor of a GBM patient.

The DLD chip was used for the analysis of neoantigen-specific CD8+ T cells, collected from the brain tumor of a GBM patient. The antigens (in this case, containing mutations, and so called neoantigens), that defined the nanoparticle-barcoded NACS library are given at top left of FIG. 13. Tumor infiltrating lymphocytes (TILS) were collected from a GBM patient tumor (at recurrence following chemotherapy and radiation therapy) and expanded in vitro. Approximately 5000 CD8+ T cells were evaluated. The micrograph images (FIG. 13, top middle image) show barcoded T cells in the microfluidic device traps, followed by fluorescence images through the three steps of barcode deciphering. Four of the cells shown exhibit 'yellow red yellow' barcodes, while a fifth exhibits a 'yellow green yellow' barcode. The barcodes for #5 and #8 library elements are shown at far right. The plot shows the frequency of detection of neoantigen-specific T cell populations. Three populations (#2, #5, #8) are detected above background noise (0.04%), with one major population (#5). For population #5, 13 neoantigen-specific T cells were detected (0.26%).

These data evidence that the methodologies and devices described in detail herein are capable of identification of rare populations of antigen-specific T cells from a sample with a high throughput method using the microfluidic device provided herein.

Other Embodiments

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

The invention claimed is:

1. A microfluidic device comprising:
a sample inlet;
a separation channel comprising an array of obstacles disposed within the separation channel, wherein said array of obstacles comprises a plurality of rows of obstacles and a plurality of columns of obstacles, said plurality of rows of obstacles extending at an angle relative to the average flow direction of said separation channel;
one or more capture areas each comprising one or more capture channels, wherein each capture channel comprises a trap region and an outflow region, provided in an arrangement in which the width of the trap region is greater than a width at the outflow region and wherein capture channel is configured to allow flow of fluid from the trap region through the outflow region and is configured to prevent a cell in the trap region from translocating through the outflow region due to a steric hindrance of the cell; and
an outlet,
wherein the separation channel is disposed between and in fluidic communication with the sample inlet and the one or more capture areas, and wherein the one or more capture areas is disposed between and in fluidic communication with the separation channel and the outlet.

2. The microfluidic device of claim 1, wherein said plurality of obstacles is adapted to separate nanoparticles bound to T cells from unbound nanoparticles upon flow of a sample through said separation channel.

3. The microfluidic device of claim 1, wherein said array of obstacles are fixed in position and separated by gaps arranged so that the particles having a size at or above the critical size deflect towards a first wall of said separation channel during flow of said heterogeneous fluid sample through said separation channel.

4. The microfluidic device of claim 1, wherein said angle relative to the average flow direction of the separation channel is about 1 degree to about 15 degrees, from about 3 degrees to about 12 degrees, from about 4 degrees to about 8 degrees, or from about 5 degrees to about 7 degrees.

5. The microfluidic device of claim 1, wherein said plurality of rows of obstacles comprises a gap between adjacent rows of from about 8 μm to about 15 μm.

6. The microfluidic device of claim 1, wherein said plurality of columns of obstacles comprise a gap between adjacent columns of from about 8 μm to about 15 μm.

7. The microfluidic device of claim 1, further comprising a mixing channel disposed between and in fluidic communication with the separation channel and the one or more capture areas.

8. The microfluidic device of claim 7, wherein said mixing channel is serpentine-shaped.

9. The microfluidic device of claim 1, further comprising a disbursement channel disposed between and in fluidic communication with the mixing channel and the one or more capture areas.

10. The microfluidic device of claim 9, wherein said disbursement channel comprises a branched network of channels extending from the mixing channel into two or more channels comprising said one or more capture areas.

11. The microfluidic device of claim 1, wherein said one or more capture areas are disposed at bends along a serpentine-shaped channel of said microfluidic device.

12. The microfluidic device of claim 1, wherein said critical size is a diameter from 2 to 6 μm.

13. The microfluidic device of claim 1, wherein said trap region of said capture channel comprises a width of about 12 μm, from 10 to 14 μm, from 8 to 16 μm, or from 8 to 12 μm.

14. The microfluidic device of claim 1, wherein said trap region is adapted to capture a T cell.

15. The microfluidic device of claim 1, further comprising a cell prefocusing region adapted to disperse particles in a fluid flowing through said microfluidic device having a size at or above a critical size in a differential manner deviating from the direction of fluid flow towards said one or more capture channels.

16. A microfluidic device comprising:
a sample inlet;
a separation channel comprising an array of obstacles disposed within the separation channel, wherein said array of obstacles comprises a plurality of rows of obstacles and a plurality of columns of obstacles, said plurality of rows of obstacles extending at an angle of about 6 degrees relative to the average flow direction of said separation channel and comprising a gap between adjacent obstacles of from about 8 μm to about 15 μm, and said plurality of columns of obstacles comprising a gap between adjacent obstacles of from about 8 m to about 15 μm;
a serpentine-shaped mixing channel;
a disbursement channel;
one or more cell isolation channels comprising one or more capture areas each comprising one or more capture channels, wherein each capture channel comprises a trap region and an outflow region, wherein the width of the trap region is about 12 μm, the width of the outflow region is about 2 μm, and the length of the outflow region is about 8-15 μm,
wherein said trap region of said capture channel is configured to capture a T cell from a sample fluid flowing through said capture channel, and wherein said capture channel is configured to allow flow of said sample fluid through said outflow region and is configured to prevent a T cell in the trap region from translocating through the outflow region of said capture channel due to a steric hindrance of the cell; and
an outlet,
wherein the separation channel is disposed between and in fluidic communication with the sample inlet and the one or more capture areas, wherein the serpentine-shaped mixing channel is disposed between and in fluidic communication with the separation channel and disbursement channel, wherein the disbursement channel comprises a branched network of channels extending from the mixing channel or the separation channel into two or more cell isolation channels or two or more mixing channels, and wherein the one or more cell isolation channels are disposed between and in fluidic communication with the separation channel and the outlet.

17. The microfluidic device of claim 1, wherein said outflow region of said capture channel comprises a length of about 8-15 μm.

18. The microfluidic device of claim 1, further comprising a sensor for detecting a signal from said trap region of said capture channel.

19. The microfluidic device of claim 1,
   wherein the angle is about 6 degrees, and
   wherein the width of the trap region is about 12 μm, the width of the outflow region is about 2 μm, and the length of the outflow region is about 8 to about 15 μm.

* * * * *

UNITED STATES PATENT AND TRADEMARK OFFICE
CERTIFICATE OF CORRECTION

Page 1 of 3

PATENT NO. : 11,384,327 B2
APPLICATION NO. : 16/347559
DATED : July 12, 2022
INVENTOR(S) : Songming Peng et al.

It is certified that error appears in the above-identified patent and that said Letters Patent is hereby corrected as shown below:

On the Title Page

Page 2, Column 2 (Item (56) Other Publications), Line 8, delete "-67"," and insert -- -B7", --.

In the Drawings

Sheet 16 of 20 (FIG. 9 (Cont.)), Line 2 (approx.), delete "flourescence" and insert -- fluorescence --.

In the Specification

Column 3, Line 3, delete "channel" and insert -- channel. --.

Column 3, Line 31-32, delete "about about" and insert -- about --.

Column 4, Line 53, delete "channel, and" and insert -- channel; and --.

Column 5, Line 55, delete "barcoded cells" and insert -- barcoded T cells --.

Column 6, Line 46, delete "channel channel" and insert -- channel --.

Column 8, Line 1, delete "microfluidic, device" and insert -- microfluidic device --.

Column 8, Line 2, delete "prefocusing," and insert -- prefocusing --.

Column 8, Line 36, delete "DM" and insert -- DLD --.

Column 9, Line 10, delete "1. MILE" and insert -- 1 MHC --.

Column 9, Line 20, delete "NP-MACS" and insert -- NP-NACS --.

Signed and Sealed this
Twenty-second Day of November, 2022

Katherine Kelly Vidal
*Director of the United States Patent and Trademark Office*

CERTIFICATE OF CORRECTION (continued)

Column 9, Line 21, delete "NP-MACS" and insert -- NP-NACS --.

Column 9, Line 48, delete "of a Mart" and insert -- of Mart --.

Column 10, Line 34, delete "DID" and insert -- DLD --.

Column 11, Line 15, delete "antigens neoantigens)." and insert -- antigens (i.e., neoantigens). --.

Column 11, Line 25, delete "al, 2014," and insert -- al., 2014, --.

Column 12, Line 48, delete "MACS" and insert -- NACS --.

Column 14, Line 16, delete "stranded. DNA" and insert -- stranded DNA --.

Column 16, Line 49, delete "captured cell" and insert -- captured T cell --.

Column 16, Line 60, delete "MACS" and insert -- NACS --.

Column 18, Line 2, delete "½" and insert -- ⅓ --.

Column 19, Line 34, delete "direction" and insert -- direction. --.

Column 20, Line 25, delete "arrays" and insert -- (i.e., arrays --.

Column 20, Line 59, delete "DUD" and insert -- DLD --.

Column 21, Line 37, delete "barcoded. T" and insert -- barcoded T --.

Column 21, Line 54, delete "deign" and insert -- design --.

Column 21, Line 57, delete "vs," and insert -- vs. --.

Column 24, Line 42, delete "(LICA)," and insert -- (LIGA), --.

Column 25, Line 43-44, delete "hemocytomer" and insert -- hemocytometer --.

Column 25, Line 50, delete "inclubating" and insert -- incubating --.

Column 26, Line 6, delete "NT-" and insert -- NP- --.

Column 28, Line 23, delete "dyes)" and insert -- dyes). --.

Column 29, Line 63, delete "Marti" and insert -- Mart-1 --.

Column 31, Line 38, delete "ULD" and insert -- DLD --.

Column 31, Line 40, delete "DLI)" and insert -- DLD --.

In the Claims

Column 34, Line 38, In Claim 16, delete "8 m" and insert -- 8 μm --.